(12) United States Patent
Jeanguenat et al.

(10) Patent No.: US 7,601,743 B2
(45) Date of Patent: Oct. 13, 2009

(54) CYANO ANTHRANILAMIDE INSECTICIDES

(75) Inventors: Andre Jeanguenat, Basel (CH);
Anthony O'Sullivan, Basel (CH);
Michael Muehlebach, Basel (CH);
Stephan Trah, Basel (CH); Roger Graham Hall, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 11/911,887

(22) PCT Filed: Apr. 18, 2006

(86) PCT No.: PCT/EP2006/003504

§ 371 (c)(1),
(2), (4) Date: Oct. 18, 2007

(87) PCT Pub. No.: WO2006/111341

PCT Pub. Date: Oct. 26, 2006

(65) Prior Publication Data

US 2008/0182750 A1 Jul. 31, 2008

(30) Foreign Application Priority Data

Apr. 20, 2005 (GB) .................. 0507989.2
Dec. 8, 2005 (GB) .................. 0525060.0

(51) Int. Cl.
*C07D 401/04* (2006.01)
*A61K 31/4439* (2006.01)

(52) U.S. Cl. .............. 514/341; 544/92; 546/275.4; 548/374.1

(58) Field of Classification Search .......... None
See application file for complete search history.

(56) References Cited

U.S. PATENT DOCUMENTS 6,747,047 B2 * 6/2004 Lahm et al. ........... 514/341
7,247,647 B2 * 7/2007 Hughes et al. .......... 514/341
7,276,601 B2 * 10/2007 Taylor ................ 544/92
7,339,057 B2 * 3/2008 Taylor ................ 544/92
2009/0133318 A1 * 5/2009 Lahm .................. 43/131

FOREIGN PATENT DOCUMENTS

| WO | 01/70671 A | 9/2001 |
| WO | 03/015518 A | 2/2003 |
| WO | 2004/067528 A | 8/2004 |
| WO | WO 2004/011030 | * 12/2004 |
| WO | 2005/085234 A | 9/2005 |

OTHER PUBLICATIONS

Huang et al., Chemical Abstracts, 96:143423, 1982.*

* cited by examiner

*Primary Examiner*—Fiona T Powers
(74) *Attorney, Agent, or Firm*—James Cueva

(57) ABSTRACT

Compounds of formula (I) wherein the substituents are as defined in claim 1, and the agrochemically acceptable salts and all stereoisomers and tautomeric forms of the compounds of formula I can be used as agrochemical active ingredients and can be prepared in a manner known per se.

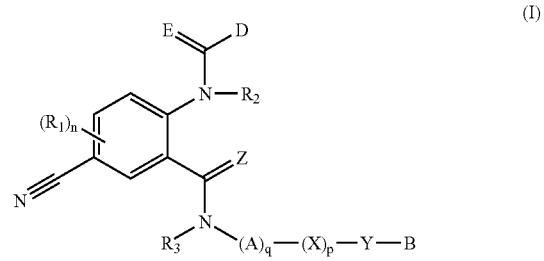

10 Claims, No Drawings

CYANO ANTHRANILAMIDE INSECTICIDES

This application is a 371 of International Application No. PCT/EP2006/003504 filed Apr. 18, 2006, which claims priority to GB 0507989.2 filed Apr. 20, 2005, and GB 0525060.0 filed Dec. 8, 2005, the contents of which are incorporated herein by reference.

The present invention relates to novel anthranilamide derivatives, to processes for their preparation, to compositions comprising those compounds, and to their use for controlling insects or representatives of the order Acarina.

Anthranilamide derivatives with insecticidal properties are known and described, for example, in WO 04/067528. There have now been found novel cyano-substituted anthranilamide derivatives with pesticidal properties, especially for the control of insects and members of the order Acarina.

The present invention accordingly relates to compounds of formula I

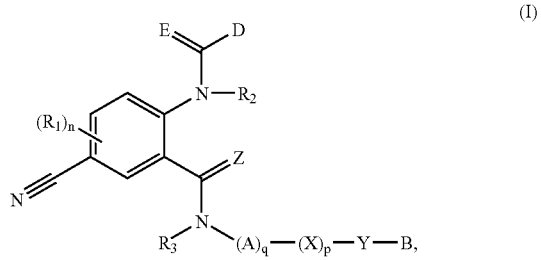

wherein
each of E and Z, which may be the same or different, represents oxygen or sulfur;

A is $C_1$-$C_6$alkylene, $C_2$-$C_6$alkenylene, $C_2$-$C_6$alkynylene, or a bivalent three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms;

and it being possible for the three- to ten-membered ring system itself and also for the $C_1$-$C_6$alkylene, $C_2$-$C_6$alkenylene and $C_2$-$C_6$alkynylene groups to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, or by
a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro;
and substituents at nitrogen atoms in the ring systems being other than halogen;

X is oxygen, NH or $C_1$-$C_4$alkyl-N;

Y is a three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms;

and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$-alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro; and substituents at nitrogen atoms in the ring systems being other than halogen;

p is 0 or 1;

q is 0 or 1;

B is a three- to four-membered ring system which is fully or partially saturated and can contain a hetero atom selected from the group consisting of nitrogen, oxygen and sulfur, and it being possible for the three- to four-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenlthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$halo-alkylsulfinyl, $C_1$-$C_6$alkylsulfonyl, $C_1$-$C_6$haloalkylsulfonyl, aminosulfonyl, $C_1$-$C_2$alkylamino-sulfonyl, N,N-di($C_1$-$C_2$alkyl)aminosulfonyl, di($C_1$-$C_4$alkyl)amino, halogen, cyano or nitro; and substituents at nitrogen atoms in the ring systems being other than halogen;

each $R_1$ independently is halogen, nitro, cyano, hydroxy, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, phenyl, benzyl or phenoxy, or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

n is 0, 1, 2 or 3;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

D is phenyl, 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

or D is a group

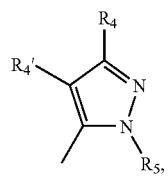

(D4)

-continued (D₁)
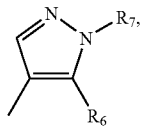

(D₂)
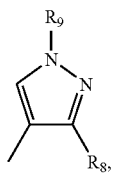

(D₃)
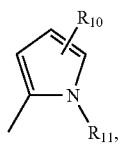

(D₅)
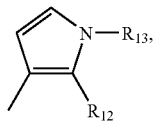

(D₆)
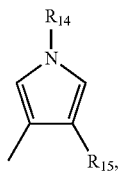

(D₇)

or (D₈)
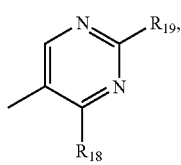

$R_4$, $R_4'$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_{C4}$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl and agronomically acceptable salts/isomers/enantiomers/tautomers/N-oxides of those compounds.

Compounds I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed. Preferred within the scope of the invention are agrochemically advantageous salts; however, the invention also encompasses salts which have disadvantage for agrochemical use, for example salts which are to bees or fish, and which are employed, for example, for the isolation or purification of free compounds I or agrochemically utilizable salts thereof. Owing to the close relationship between the compounds I in free form and in the form of their salts, for the purposes of the invention the free compounds I or their salts hereinabove and hereinbelow are respectively to be understood as including, where appropriate, the corresponding salts or the free compounds I. The same applies analogously to tautomers of compounds I and salts thereof. In general, the free form is preferred in each case.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy groups are: methoxymethoxy, methoxyethoxy, methoxypropoxy, ethoxymethoxy, ethoxyethoxy, propoxymethoxy or butoxybutoxy. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms. Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position.

The preferred substituent positions are the ortho and para positions to the ring attachment point.

Examples for B as a optionally substituted three- to four-membered ring system which is fully or partially saturated and can contain a hetero atom selected from the group consisting of nitrogen, oxygen and sulfur, are cyclopropyl, methyl-cyclopropyl, cyclopropenyl, cyclobutyl, cyclobutenyl,

According to the present invention, a three- to ten-membered, monocyclic or fused bicyclic ring system which may be partially saturated or fully saturated is, depending of the number of ring members, for example, selected from the group consisting of

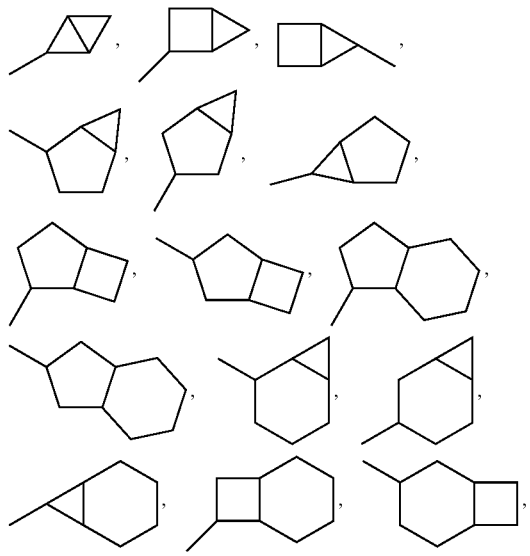

cyclopropyl, cyclobutyl, cyclopentyl, cyclohexyl, where said cycloalkylgroups for their part may be preferably unsubstituted or substituted by $C_1$-$C_6$alkyl or halogen, or is

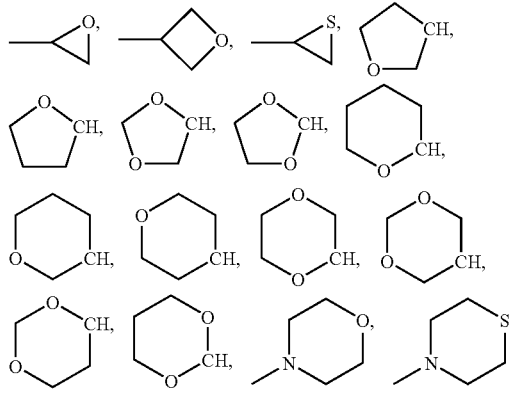

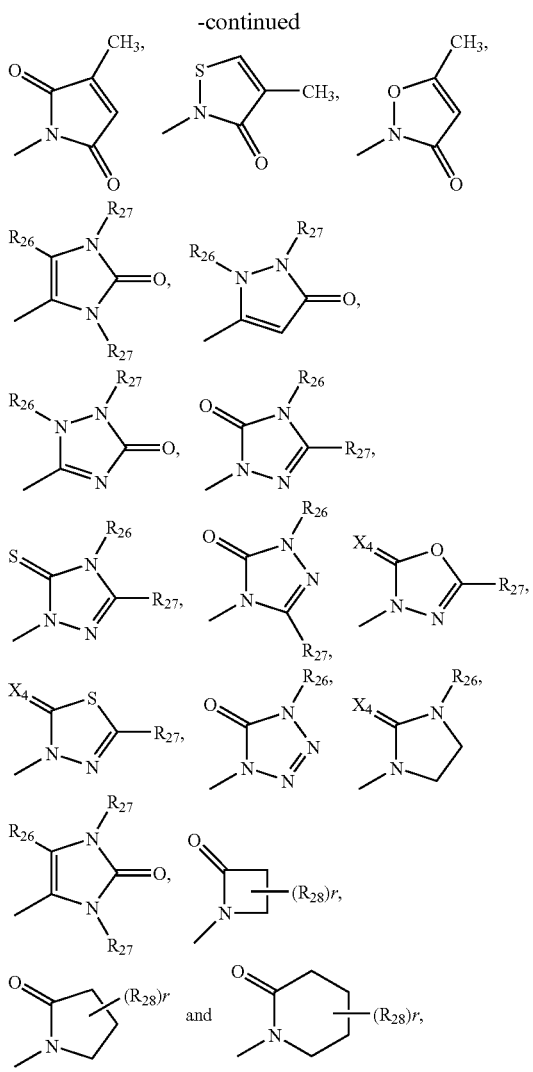

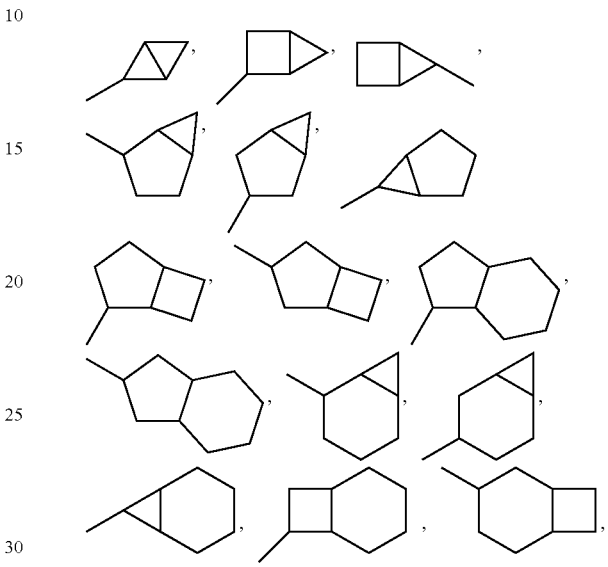

at the bonding site indicated at the bottom left. The second valence for the bivalent ring system of substituent A or Y can be located at any suitable position of the ring.

According to the present invention, a three- to ten-membered monocyclic or fused bicyclic ring system which may be aromatic, partially saturated or fully saturated is, depending of the number of ring members, for example, selected from the group consisting of cyclopropyl, cyclobutyl, cyclopentyl, cyclohexyl, where said cycloalkylgroups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isox-azolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3thienyl)-; (1-methyl-1H-imidazol-2-yl)-; (1H-imidazol-2-yl)-; (1-methyl-1H-imidazol-4-yl)-; (1methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl);(5-methyl-1,2,3-oxadiazol-4-yl)-; (1,2,3oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-mewherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions, for example as in

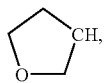

the linkage site is located at the carbon atom labelled "CH" or in a case such as, for example,

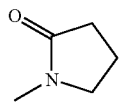

thyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyr-azinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

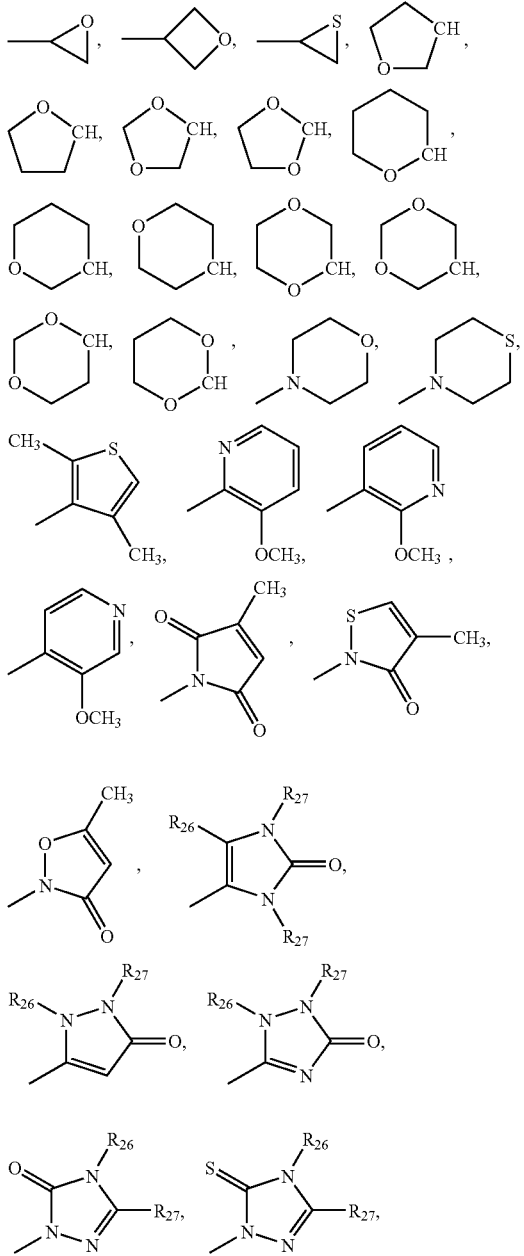

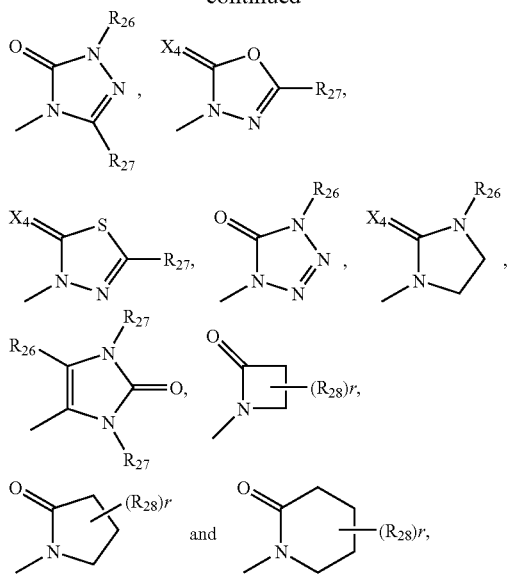

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions, for example as in

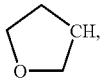

the linkage site is located at the carbon atom labelled "CH" or in a case such as, for example,

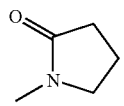

at the bonding site indicated at the bottom left.

Preference is given to subgroups of compounds of formula I wherein a) p and/or q is 0;
b) E and/or Z is oxygen; and/or
c) $R_2$ and/or $R_3$ is hydrogen and/or
d) A is a bivalent three- to six-membered saturated monocyclic ring system.

X is preferably oxygen, NH; N-Methyl or N-Ethyl.

Y is preferably $C_3$-$C_6$cycloalkyl, especially cyclopropyl.

$R_4'$ is preferably hydrogen.

Special mention should be made of compounds of formula I wherein $R_1$ is selected from $C_1$-$C_4$alkyl, halogen, $C_1$-$C_5$haloalkyl, nitro, $C_1$-$C_4$alkoxy, $C_1$-$C_4$-haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl and $C_1$-$C_4$haloalkylsulfonyl, in particular from halogen and $C_1$-$C_6$alkyl, preferably selected from methyl and halogen, most preferably selected from methyl and chloro, and n is 1 or 2, preferably 1. Preferred position of $R_1$ is meta to the group —C(Z)-N($R_3$)-A-X—Y—B.

An outstanding group of compounds of formula I comprises those compounds wherein A is $C_1$-$C_6$alkylene which may be substituted by $C_3$-$C_6$cycloalkyl, $C_2$-$C_6$alkenyl, cyano, $C_1$-$C_4$alkylthio, $C_1$-$C_4$alkylsulfonyl, $C_1$-$C_4$alkoxy, halogen or $C_1$-$C_6$haloalkyl; or A is $C_3$-$C_6$cycloalkylene. Preferably A is $C_3$-$C_6$cycloalkylene, most preferably cyclopropylene.

In preferred compounds of formula I, B is cyclopropyl, oxetanyl or cyclobutyl, preferably cyclopropyl.

Special emphasis should also be given to compounds of formula I wherein D is a group $D_1$, wherein $R_5$ is 2-pyridyl which can be substituted by halogen, preferably which is monosubstituted by chloro at the 3-position of the pyridine ring and $R_4$ is halogen preferably chloro or bromo, $C_1$-$C_6$haloalkyl, $C_1$-$C_4$haloalkoxy most preferably 2,2,2-trifluoroethoxy, preferably $C_1$-$C_6$haloalkyl, most preferably trifluoromethyl.

Preference is also given to compounds of formula I wherein in particular B is cyclopropyl or cyclobutyl which may be mono- di-, or trisubstituted by halogen, $C_1$-$C_4$alkyl, hydroxy, cyano, $C_1$-$C_4$alkoxy or $C_1$-$C_4$alkylthio; or B is CH(CH$_2$O), CH(CHMeO), CH—(CMe$_2$O), CH(CH$_2$S), CH(CH$_2$OCH$_2$), CH(CHMeOCH$_2$), CH(CMe$_2$OCH$_2$), CH(CH$_2$S—(O)$_2$CH$_2$), CH(CHMeS(O)$_2$CH$_2$), CH(CMe$_2$S(O)$_2$CH$_2$), C(Me)-(CH$_2$O), C(Me)(CHMeO), C(Me)-(CMe$_2$O), C(Me)-(CH$_2$S), C(Me)-(CH$_2$OCH$_2$), C(Me)(CHMeOCH$_2$), C(Me)-(CMe$_2$OCH$_2$), C(Me)-(CH$_2$S(O)$_2$CH$_2$), C(Me)-(CHMe-S(O)$_2$CH$_2$) or C(Me)-(CMe$_2$-S(O)$_2$CH$_2$). In especially preferred compounds of formula I B is cyclopropyl or cyclobutyl which may be substituted by halogen or methyl, in particular by chloro, bromo or methyl; most preferably B is cyclopropyl.

The process according to the invention for preparing compounds of the formula I is carried out analogously to known processes, for example those described in WO 01/70671, WO 03/016284, WO 03/015518 WO 04/033468 and WO 04/067528.

The process for the preparation of a compound of the formula I or, where appropriate, a tautomer thereof, in each case in free form or in salt form, comprises, for example, a) to prepare a compound of the formula I, in which $R_2$ is hydrogen and E and Z are oxygen, or, where appropriate, a tautomer and/or salt thereof, by reacting a compound of the formula

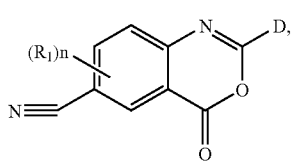

(II)

in which $R_1$, n, and D have the meanings given for the formula I, or, where appropriate, a tautomer and/or salt thereof with a compound of the formula HN($R_3$)-(A)$_q$-(X)$_p$—Y—B (III), in which $R_3$, p, q, A, X, Y and B have the meanings given for the formula I, or, where appropriate, with a tautomer and/or salt thereof or, b) to prepare a compound of the formula I, or, where appropriate, a tautomer and/or salt thereof, reacting a compound of the formula

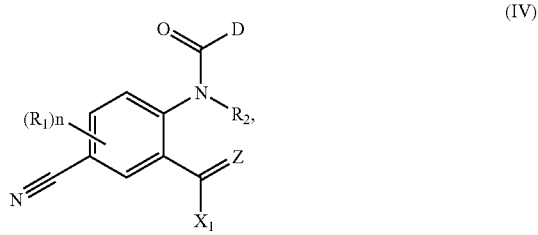

(IV)

in which $R_1$, $R_2$, n, Z and D have the meanings given for the formula I; and $X_1$ is a leaving group,or, where appropriate, a tautomer and/or salt thereof with a compound of the formula HN($R_3$)-(A)$_q$-(X)$_p$—Y—B (III), in which $R_3$, p, q, A, X, Y and B have the meanings given for the formula I, or, where appropriate, with a tautomer and/or salt thereof or, c) to prepare a compound of the formula I, or, where appropriate, a tautomer and/or salt thereof, by reacting a compound of the formula

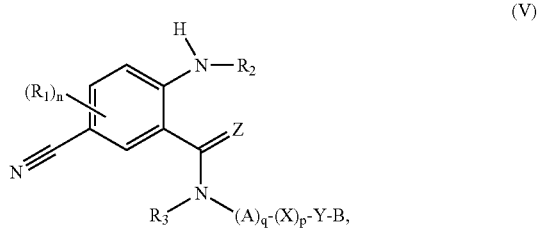

(V)

in which $R_1$, $R_2$, $R_3$, n, p, q, A, X, Y, Z and B have the meanings given for the formula I, or, where appropriate, a tautomer and/or salt thereof with a compound of the formula $X_2$C(=O)D (VI), in which $R_1$ has the meaning given for the formula I; and $X_2$ is a leaving group, or, where appropriate, with a tautomer and/or salt thereof and/or converting a compound of the formula I or, where appropriate, a tautomer thereof, in each case in free form or in salt form, into another compound of the formula I or, where appropriate, a tautomer thereof, separating an isomer mixture, which can be obtained in accordance with the process, and isolating the desired isomer and/or converting a free compound of the formula I or, where appropriate, a tautomer thereof into a salt or a salt of a compound of the formula I or, where appropriate, a tautomer thereof into the free compound of the formula I or, where appropriate, a tautomer thereof or into another salt.

The compounds of formula II are novel and are especially developed for the preparation of the compounds of formula I according to the present invention. The compounds of formula II therefore constitute a further object of the present invention. The compounds of formula II can be prepared analogously to the methods described in WO 04/111030.

The compounds of formula V are also novel and are especially developed for the preparation of the compounds of formula I according to the present invention. The compounds of formula V therefore constitute a further object of the present invention. Compounds of formula V are preferred, wherein $R_1$ is $C_1$-$C_4$alkyl, halogen, $C_1$-$C_5$haloalkyl, nitro, $C_1$-$C_4$alkoxy, $C_1$-$C_4$-haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl;

$R_2$ and $R_3$ are hydrogen;

A is $C_1$-$C_6$alkylene which may be substituted by $C_3$-$C_6$cycloalkyl, $C_2$-$C_6$alkenyl, cyano, $C_1$-$C_4$alkylthio, $C_1$-$C_4$alkylsulfonyl, $C_1$-$C_4$alkoxy, halogen or $C_1$-$C_6$haloalkyl; or A is $C_3$-$C_6$cycloalkylene;

p and q are, independently from each other, 0 or 1;

X is oxygen, NH; $NCH_3$ or $NC_2H_5$;

Y is $C_1$-$C_4$alkylene, $C_2$-$C_6$alkenylene or $C_3$-$C_6$alkinylene or, $C_1$-$C_4$alkylene, $C_2$-$C_6$alkenylene or $C_3$-$C_6$alkinylene substituted by halogen, $C_3$-$C_6$cycloalkyl, $C_1$-$C_4$alkylsulfonyl or $C_1$-$C_4$alkoxy;

and B is cyclopropyl or cyclobutyl which may be mono- di-, or trisubstituted by halogen, $C_1$-$C_4$alkyl, hydroxy, cyano, $C_1$-$C_4$alkoxy or $C_1$-$C_4$alkylthio; or B is $CH(CH_2O)$, $CH(CHMeO)$, $CH$—$(CMe_2O)$, $CH(CH_2S)$, $CH(CH_2OCH_2)$, $CH(CHMeOCH_2)$, $CH(CMe_2OCH_2)$, $CH(CH_2S$—$(O)_2CH_2)$, $CH(CHMeS(O)_2CH_2)$, $CH(CMe_2S(O)_2CH_2)$, $C(Me)$-$(CH_2O)$, $C(Me)(CHMeO)$, $C(Me)$-$(CMe_2O)$, $C(Me)$-$(CH_2S)$, $C(Me)$-$(CH_2OCH_2)$, $C(Me)(CHMeOCH_2)$, $C(Me)$-$(CMe_2OCH_2)$, $C(Me)$-$(CH_2S(O)_2CH_2)$, $C(Me)$-$(CHMe$-$S(O)_2CH_2)$ or $C(Me)$-$(CMe_2$-$S(O)_2CH_2)$, preferably B is cyclopropyl or cyclobutyl which may be mono- di-, or trisubstituted by halogen, $C_1$-$C_4$alkyl, hydroxy, cyano, $C_1$-$C_4$alkoxy or $C_1$-$C_4$alkylthio.

The process for the preparation of a compound of the formula V or, where appropriate, a tautomer thereof, in each case in free form or in salt form, comprises, for example, to prepare a compound of formula V or, where appropriate, a tautomer and/or salt thereof, by reacting a compound of the formula

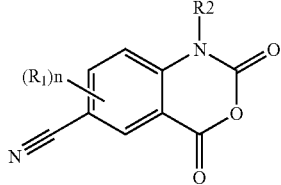

(VII)

In which $R_1$, $R_2$, n have the meanings given in the formula I with a compound of formula

$HN(R_3)$-$(A)_q$-$(X)_p$—Y—B (III), in which $R_3$, p, q, A, X, Y and B have the meanings given for the formula I, or, where appropriate, with a tautomer and/or salt thereof.

What has been said above for tautomers and/or salts of compounds I applies analogously to starting materials mentioned hereinabove and hereinbelow with regard to the tautomers and/or salts thereof.

The reactions described hereinabove and hereinbelow are carried out in a manner known per se, for example in the absence or, normally, in the presence of a suitable solvent or diluent or of a mixture of these, the process being carried out, as required, with cooling, at room temperature or with heating, for example in a temperature range of from approximately −80° C. to the boiling point of the reaction mixture, preferably from approximately −20° C. to approximately +150° C., and, if required, in a sealed vessel, under reduced, normal or elevated pressure, in an inert gas atmosphere and/or under anhydrous conditions. Especially advantageous reaction conditions can be seen from the examples.

Unless otherwise specified, the starting materials mentioned hereinabove and hereinbelow, which are used for the preparation of the compounds I or, where appropriate, the tautomers thereof, in each case in free form or in salt form, are known or can be prepared by methods known per se, for example in accordance with the information given below.

Variant a)

The reactants can be reacted with each other as such, i.e. without addition of a solvent or diluent, for example in the melt. In most cases, however, it is advantageous to add an inert solvent or diluent or a mixture of these. Examples of such solvents or diluents which may be mentioned are: aromatic, aliphatic and alicyclic hydrocarbons and halohydrocarbons such as benzene, toluene, xylene, mesitylene, tetralin, chlorobenzene, dichlorobenzene, bromo-benzene, petroleum ether, hexane, cyclohexane, dichloromethane, trichloromethane, tetra-chloromethane, dichloroethane, trichloroethene or tetrachloroethene; esters such as ethyl acetate; ethers such as diethyl ether, dipropyl ether, diisopropyl ether, dibutyl ether, tert-butyl methyl ether, ethyleneglycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides such as N,N-di-methylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide.

The reaction is advantageously carried out in a temperature range from approximately −80° C. to approximately +140° C., preferably from approximately −30° C. to approximately +100° C., in many cases in the range between room temperature and approximately +80° C.

Variant b)

Examples of suitable leaving groups $X_1$ in the compounds IV are hydroxy, $C_1$-$C_8$alkoxy, halo-$C_1$-$C_8$alkoxy, $C_1$-$C_8$alkanoyloxy, mercapto, $C_1$-$C_8$alkylthio, halo-$C_1$-$C_8$alkylthio, $C_1$-$C_8$alkylsulfonloxy, halo-$C_1$-$C_8$alkylsulfonyloxy, benzenesulfonyloxy, toluenesulfonyloxy and halogen, such as chlorine. Preferred are hydroxy, $C_1$-$C_8$alkoxy and chlorine.

The reactants can be reacted with each other as such, i.e. without adding a solvent or diluent. In most cases, however, it is advantageous to add an inert solvent or diluent or a mixture of these. Examples of suitable solvents or diluents are of the type described under variant a).

The reaction is advantageously carried out in a temperature range from approximately −80° C. to approximately +140° C., preferably from approximately −20° C. to approximately +100° C., in many cases in the range between room temperature and the reflux temperature of the reaction mixture.

Variant c)

Examples of suitable leaving groups $X_2$ in the compounds VI are hydroxy, $C_1$-$C_8$alkoxy, halo-$C_1$-$C_8$alkoxy, $C_1$-$C_8$alkanoyloxy, mercapto, $C_1$-$C_8$alkylthio, halo-$C_1$-$C_8$alkylthio, $C_1$-$C_8$-alkylsulfonyloxy, halo-$C_1$-$C_8$alkylsulfonyloxy, benzenesulfonyloxy, toluenesulfonyloxy and halogen, such as chlorine. Preferred are hydroxy and chlorine.

The reactants can be reacted in the presence of a base. Examples of suitable bases for facilitating the detachment of HX$_2$ are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. Examples of suitable solvents or diluents are of the type described under variant a). If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between room temperature and approximately +80° C.

A compound I can be converted in a manner known per se into another compound I by replacing one or more substituents of the starting compound I in the customary manner by (an)other substituent(s) according to the invention.

For example,
in compounds I, in which R$_2$ is hydrogen, this hydrogen R$_2$ can be replaced by a substituent R$_2$, which is different from hydrogen; or
in compounds I, in which R$_3$ is hydrogen, this hydrogen R$_3$ can be replaced by a substituent R$_3$, which is different from hydrogen.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds according to the invention and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,
Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp. and Tetranychus spp.;

from the order Anoplura, for example,
Haematopinus spp., Linognathus spp., Pediculus spp., Pemphigus spp. and Phylloxera spp.;

from the order Coleoptera, for example,
Agriotes spp., Anthonomus spp., Atomaria linearis, Chaetocnema tibialis, Cosmopolites spp., Curculio spp., Dermestes spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Diptera, for example,
Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.;

from the order Heteroptera, for example,
Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;

from the order Homoptera, for example,
Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Parlatoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

from the order Hymenoptera, for example,
Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;

from the order Isoptera, for example,
Reticulitermes spp.;

from the order Lepidoptera, for example,
Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambiguella, Cnaphalocrocis spp., Cnephasia spp., Cochylis spp., Coleophora spp., Crocidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Heliothis spp., Hellula undalis, Hyphantria cunea, Keiferia lycopersicella, Leucoptera scitella, Lithocollethis spp., Lobesia botrana, Lymantria spp., Lyonetia spp., Malacosoma spp., Mamestra brassicae, Manduca sexta, Operophtera spp., Ostrinia nubilalis, Pammene spp., Pandemis spp., Panolis flammea, Pectinophora gossypiela, Phthorimaea operculella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

from the order Mallophaga, for example,
Damalinea spp. and Trichodectes spp.;

from the order Orthoptera, for example,
Blatta spp., Blattella spp., Gryllotalpa spp., Leucophaea maderae, Locusta spp., Periplaneta spp. and Schistocerca spp.;

from the order Psocoptera, for example,
Liposcelis spp.;

from the order Siphonaptera, for example,
Ceratophyllus spp., Ctenocephalides spp. and Xenopsylla cheopis;

from the order Thysanoptera, for example,
Frankliniella spp., Hercinothrips spp., Scirtothrips aurantii, Taeniothrips spp., Thrips palmi and Thrips tabaci; and from the order Thysanura, for example,
Lepisma saccharina.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; *Lauraceae*, such as avocado, *Cinnamonium* or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca*(preferably in vegetables, vineyards), *Leptinotarsa* (preferably in potatoes) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Boligard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIA toxin); Nature-Gard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NU00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compounds according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders *Nematocerina* and *Brachycerina*, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass *Acaria (Acarida)* and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (*Prostigmata*) and *Acaridida* (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds according to the invention are also suitable for protecting against insect infestation in the case of materials such as wood, textiles, plastics, adhesives, glues, paints, paper and card, leather, floor coverings and buildings.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a pnonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants(% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

| Emulsifiable concentrates: | |
|---|---|
| active ingredient: | 1 to 95%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granulates: | |
| active ingredient: | 0.5 to 30%, preferably 3 to 15% |
| solid carrier: | 99.5 to 70%, preferably 97 to 85% |

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

PREPARATION EXAMPLES

Example P1

Preparation of 2-(3-Chloro-pyridin-2-yl)-5-trifluoromethyl-2H-pyrazole-3-carboxylic acid [2-(bicyclopropyl-1-ylcarbamoyl)-4-cyano-6-methyl-phenyl]-amide (A.1.1)

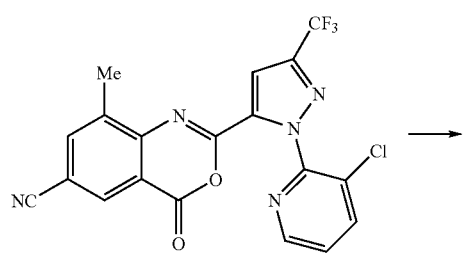

-continued

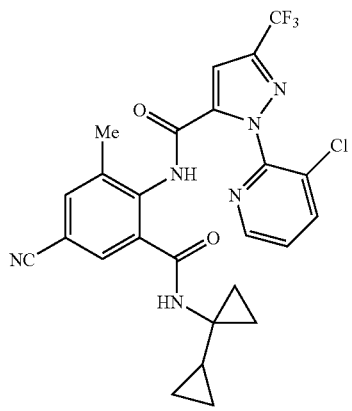

To a solution of 2-[2-(3-chloro-pyridin-2-yl)-5-trifluoromethyl-2H-pyrazol-3-yl]-8-methyl-4-oxo-4H-benzo[d][1,3]oxazine-6-carbonitrile (1.2 g, 2,8 mmol) (prepared according to WO 04/067528) in tetrahydrofuran (40 ml), is added bicyclopropyl-1-ylamine hydrochloride (0.6 g, 4.2 mmol) and 1.2 ml (8.4 mmol) triethylamine, and the solution is heated at a temperature of 60° C. for 8 h. The solution is cooled down to ambient temperature and the solvent is evaporated. Then the mixture is triturated in 100 ml water and the crystals are washed with water and ether to afford 0.85 g of the title compound. The mother liquor is evaporated and a second crop of crystals is obtained by crystallisation in diisopropylether to afford 0.46 g of the title compound (F: 270-272° C.).

Example P2

Preparation of 2-(3-Chloro-pyridin-2-yl)-5-trifluoromethyl-2H-pyrazole-3-carboxylic acid [2-(bicyclopropyl-1-ylcarbamoyl)-4-cyano-6-methyl-phenyl]-amide (A.1.1)

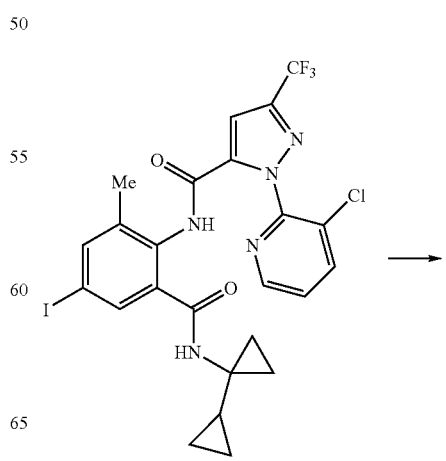

-continued

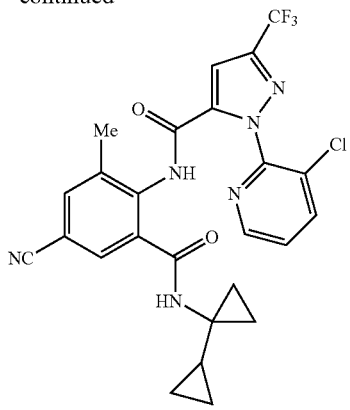

To a solution of 3.29 g (5.23 mmol) 2-(3-chloro-pyridin-2-yl)-5-trifluoromethyl-2H-pyrazole-3-carboxylic acid [2-(bicyclopropyl-1 -ylcarbamoyl)-4-iodo-6-methyl-phenyl]-amide in 50 ml tetrahydrofuran is added 1.19 g (6.25 mmol) CuI, 0.30 g tetrakis(triphenylphosphine) palladium and 2.78 g (31.0 mmol) CuCN. The mixture is heated 1 h at 80° C. and turns dark green. After cooling down, the mixture is filtered on Hyflo and evaporated. The residue is dissolved in 15 ml DMF and poured into 100 ml water containing 5 g NaHCO₃. After 30 min stirring, the crystals are filtered, washed with water and a mixture of hexane/acetone (1:3) to afford 2.8 g of the title compound.

Preparation of 2-(3-Chloro-pyridin-2-yl)-5-trifluoromethyl-2H-pyrazole-3-carboxylic acid [2-(bicyclopropyl-1-ylcarbamoyl)-4-iodo-6-methyl-phenyl]-amide

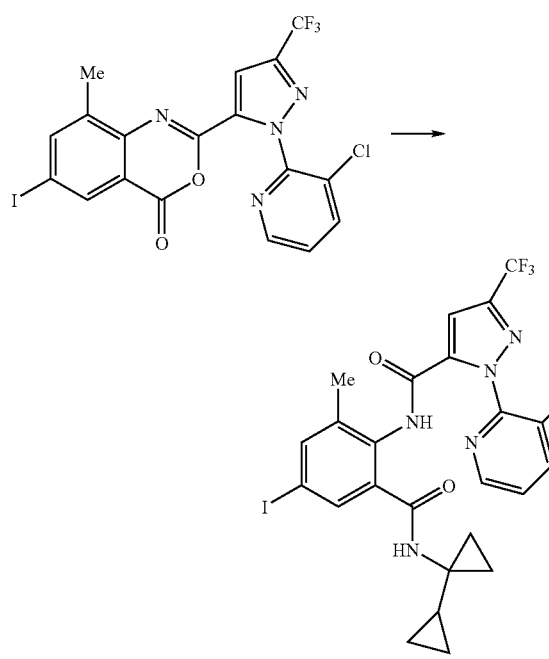

2.08 g (3.91 mmol) (2-[2-(3-chloro-pyridin-2-yl)-5-trifluoromethyl-2H-pyrazol-3-yl]-8-hydroxy-6-iodo-benzo[d][1,3]oxazin-4-one (prepared according to WO 04/067528), 0.6 g (4.50 mmol) bicyclopropyl-1-ylamine hydrochloride and 0.63 ml (4.50 mmol) triethylamine in 20 ml THF are heated 20 h at reflux. After cooling down, the precipitate is filtered and the mother liquor is evaporated. The residue is dissolved in 5 ml DMF and poured into 40 ml water. The crystals formed are filtered and purified by flash-chromatography (dichloromethane 40, diethylether 1) to afford 1.85 g title compound. ¹H-NMR (CDCl₃, 400 MHz. ppm): 0.11 (q, 2H), 0.45 (q, 2H), 0.62 (s, 4H), 1.4 (m, 1H), 2.10 (s, 3H), 6.50 (s, 1H), 7.40 (m, 2H), 7.51 (s, 1H), 7.77 (s, 1H), 7.85 (dd, 1H), 8.49 (m, 1H), 10.45 (s, 1H).

Preparation of 2-Amino-N-bicyclopropyl-1-yl-5-cyano-3-methyl-benzamide

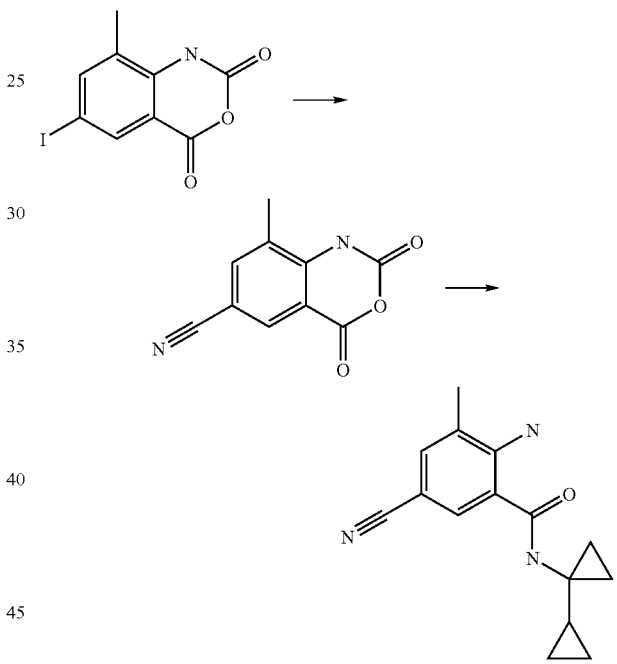

600 mg (1.98 mmol) 6-iodo-8-methyl-1H-benzo[d][1,3]oxazine-2,4-dione (prepared according to known procedures, see G. M. Coppola, *Synthesis,* 1980, 505), 212 mg (2.37 mmol) CuCN, 377 mg (1.98 mmol) CuI and 114 mg tetrakis(triphenylphosphine) palladium in 60 ml THF are heated 5 h at reflux. After cooling down, the mixture is filtered on Hyflo. The organic phase is washed with water and evaporated. The residue is crystallized from a mixture of dichloromethane, ethyl acetate and hexane to afford 245 mg 8-methyl-2,4-dioxo-1,4-dihydro-2H-benzo[d][1,3]oxazine-6-carbonitrile, which is directly used in the next step.

236 mg (1.16 mmol) 8-methyl-2,4-dioxo-1,4-dihydro-2H-benzo[d][1,3]oxazine-6-carbonitrile, 234 mg (1.75 mmol) bicyclopropyl-1-ylamine hydrochloride and 177 mg (1.75 mmol) triethylamine in 25 ml THF are heated 4 h at reflux. The mixture is cooled down and evaporated. The residue is dissolved in ethyl acetate and extracted with water. After

Preparation of bicyclopropyl-1-ylamine

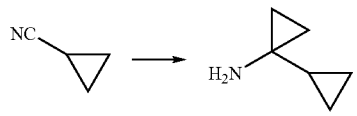

93.2 ml (328 mmol) Ti(OiPr)$_4$ is added to a solution of 20 g (298 mmol) cyclopropane carbonitrile in 300 ml ether. Then the solution is cooled down to −78° C. and 199 ml (596 mmol) ethylmagnesium bromide solution (3 M in ether) are slowly added. After 10 min at −78° C., the slurry is allowed to warm up to ambient temperature and stirred for 1 hour. Then 84.6 g (595 mmol) BF$_3$.OEt$_2$ is added and the mixture is stirred at ambient temperature for 18 hours. To this mixture, 600 ml NaOH 2N is slowly added at a temperature of 0° C. The organic phase is separated and extracted with 600 ml HCl 2N. The water phase is evaporated and the residue is triturated in ether to afford 30.9 g of the title compound as an hydrochloride salt.

The examples which follow are intended to illustrate the invention and show preferred compounds of formula I. Me means the methyl group. Et means the ethyl group. If no definition for substituent X is given, then p is 0, if X is a substituent, then p is 1. If no definition for substituent A is given, then q is 0, if A is a substituent, then q is 1. The group C(CH$_2$CH$_2$) for the substituent Y means cyclopropyl with two free valences:

TABLE A

Compounds of formula Ia:

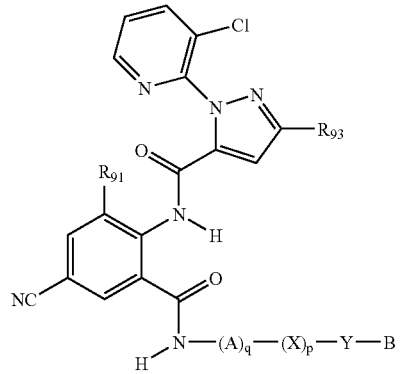

(Ia)

| Comp. No. | R$_{91}$ | R$_{93}$ | A | X | Y | B |
|---|---|---|---|---|---|---|
| A.1.1 | Me | CF$_3$ | — | — | C(CH$_2$CH$_2$) | cyclo-propyl |
| A.1.2 | Cl | CF$_3$ | — | — | C(CH$_2$CH$_2$) | cyclo-propyl |
| A.1.3 | Br | CF$_3$ | — | — | C(CH$_2$CH$_2$) | cyclo-propyl |
| A.1.4 | Me | Cl | — | — | C(CH$_2$CH$_2$) | cyclo-propyl |
| A.1.5 | Cl | Cl | — | — | C(CH$_2$CH$_2$) | cyclo-propyl |
| A.1.6 | Br | Cl | — | — | C(CH$_2$CH$_2$) | cyclo-propyl |
| A.1.7 | Me | Br | — | — | C(CH$_2$CH$_2$) | cyclo-propyl |
| A.1.8 | Cl | Br | — | — | C(CH$_2$CH$_2$) | cyclo-propyl |
| A.1.9 | Br | Br | — | — | C(CH$_2$CH$_2$) | cyclo-propyl |
| A.1.10 | Me | OCHF$_2$ | — | — | C(CH$_2$CH$_2$) | cyclo-propyl |
| A.1.11 | Cl | OCHF$_2$ | — | — | C(CH$_2$CH$_2$) | cyclo-propyl |
| A.1.12 | Br | OCHF$_2$ | — | — | C(CH$_2$CH$_2$) | cyclo-propyl |
| A.1.13 | Me | OCH$_2$CF$_3$ | — | — | C(CH$_2$CH$_2$) | cyclo-propyl |
| A.1.14 | Cl | OCH$_2$CF$_3$ | — | — | C(CH$_2$CH$_2$) | cyclo-propyl |
| A.1.15 | Br | OCH$_2$CF$_3$ | — | — | C(CH$_2$CH$_2$) | cyclo-propyl |
| A.1.16 | Me | CHF$_2$ | — | — | C(CH$_2$CH$_2$) | cyclo-propyl |
| A.1.17 | Cl | CHF$_2$ | — | — | C(CH$_2$CH$_2$) | cyclo-propyl |
| A.1.18 | Br | CHF$_2$ | — | — | C(CH$_2$CH$_2$) | cyclo-propyl |
| A.1.19 | Me | CH$_2$CF$_3$ | — | — | C(CH$_2$CH$_2$) | cyclo-propyl |
| A.1.20 | Cl | CH$_2$CF$_3$ | — | — | C(CH$_2$CH$_2$) | cyclo-propyl |
| A.1.21 | Br | CH$_2$CF$_3$ | — | — | C(CH$_2$CH$_2$) | cyclo-propyl |
| A.1.22 | Me | CF$_3$ | — | — | CH(cyclo-propyl) | cyclo-propyl |
| A.1.23 | Me | CF$_3$ | — | — | C(CH$_2$CH$_2$) | cyclo-propyl |
| A.1.24 | Me | CF$_3$ | — | — | C(CH$_2$CHF) | cyclo-propyl |
| A.1.25 | Me | CF$_3$ | — | — | C(CH$_2$CF$_2$) | cyclo-propyl |
| A.1.26 | Me | CF$_3$ | — | — | C(CH$_2$CHCl) | cyclo-propyl |
| A.1.27 | Me | CF$_3$ | — | — | C(CH$_2$CFCl) | cyclo-propyl |

(purification on a short path of silicagel, 63 mg of the title compound are isolated as yellow crystals. F: 171-172° C.)

TABLE A-continued

Compounds of formula Ia:

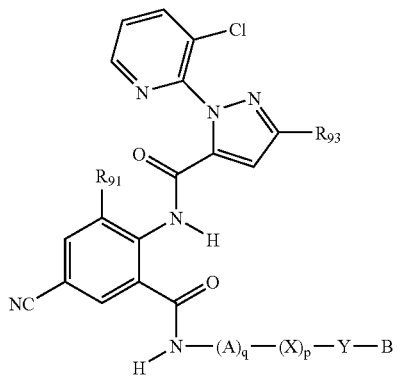

(Ia)

| Comp. No. | $R_{91}$ | $R_{93}$ | A | X | Y | B |
|---|---|---|---|---|---|---|
| A.1.28 | Me | $CF_3$ | — | — | $C(CH_2CCl_2)$ | cyclo-propyl |
| A.1.29 | Me | $CF_3$ | — | — | $C(CH_2CHBr)$ | cyclo-propyl |
| A.1.30 | Me | $CF_3$ | — | — | $C(CH_2CBr_2)$ | cyclo-propyl |
| A.1.31 | Me | $CF_3$ | $C(CH_2CHMe)$ | — | $C(CH_2CHMe)$ | cyclo-propyl |
| A.1.32 | Me | $CF_3$ | — | — | $C(CH_2CMe_2)$ | cyclo-propyl |
| A.1.33 | Me | $CF_3$ | — | — | $C(CH_2CHEt)$ | cyclo-propyl |
| A.1.34 | Me | $CF_3$ | — | — | $C(CH_2CEt_2)$ | cyclo-propyl |
| A.1.35 | Me | $CF_3$ | — | — | $C(CH_2OCH_2)$ | cyclo-propyl |
| A.1.36 | Me | $CF_3$ | — | — | $C(CH_2S(O)_2—CH_2$ | cyclo-propyl |
| A.1.37 | Me | $CF_3$ | $C(CH_2CH_2)$ | O | $C(CH_2CH_2)$ | cyclo-propyl |
| A.1.38 | Me | $CF_3$ | $CH_2$ | $CH_2$ | $C(CH_2CH_2)$ | cyclo-propyl |
| A.1.39 | Me | $CF_3$ | $CH_2$ | O | CH-(cyclo-propyl) | cyclo-propyl |
| A.1.40 | Me | $CF_3$ | $CH_2$ | O | $CH(CH_2S—(O)_2Me)$ | cyclo-propyl |
| A.1.41 | Me | $CF_3$ | $CH_2$ | O | $CH(CH_2O-Me)$ | cyclo-propyl |
| A.1.42 | Me | $CF_3$ | $CH_2$ | O | $C(CH_2CH_2)$ | cyclo-propyl |
| A.1.43 | Me | $CF_3$ | $CH_2$ | O | $C(CH_2CHF)$ | cyclo-propyl |
| A.1.44 | Me | $CF_3$ | $CH_2$ | O | $C(CH_2CF_2)$ | cyclo-propyl |
| A.1.45 | Me | $CF_3$ | $CH_2$ | O | $C(CH_2CHCl)$ | cyclo-propyl |
| A.1.46 | Me | $CF_3$ | $CH_2$ | O | $C(CH_2CFCl)$ | cyclo-propyl |
| A.1.47 | Me | $CF_3$ | $CH_2$ | O | $C(CH_2CCCl_2)$ | cyclo-propyl |
| A.1.48 | Me | $CF_3$ | $CH_2$ | O | $C(CH_2CHBr)$ | cyclo-propyl |
| A.1.49 | Me | $CF_3$ | $CH_2$ | O | $C(CH_2CBr_2)$ | cyclo-propyl |
| A.1.50 | Me | $CF_3$ | $CH_2$ | O | $C(CH_2CHMe)$ | cyclo-propyl |
| A.1.51 | Me | $CF_3$ | $CH_2$ | O | $C(CH_2CMe_2)$ | cyclo-propyl |
| A.1.52 | Me | $CF_3$ | $CH_2$ | O | $C(CH_2CHEt)$ | cyclo-propyl |
| A.1.53 | Me | $CF_3$ | $CH_2$ | O | $C(CH_2C-Et_2)$ | cyclo-propyl |
| A.1.54 | Me | $CF_3$ | — | — | $C(CH_2CH_2)$ | 1-fluoro-cyclo-propyl |
| A.1.55 | Me | $CF_3$ | — | — | $C(CH_2CH_2)$ | 1-chloro-cyclo-propyl |
| A.1.56 | Me | $CF_3$ | — | — | $C(CH_2CH_2)$ | 1-bromo-cyclo-propyl |
| A.1.57 | Me | $CF_3$ | — | — | $C(CH_2CH_2)$ | 1-methyl--cyclo-propyl |
| A.1.58 | Me | $CF_3$ | — | — | $C(CH_2CH_2)$ | 1-ethyl-cyclo-propyl |
| A.1.59 | Me | $CF_3$ | — | — | $C(CH_2CH_2)$ | 1-cyano-cyclo-propyl |
| A.1.60 | Me | $CF_3$ | — | — | $C(CH_2CH_2)$ | 1-methyl--thiocyclo-propyl |
| A.1.61 | Me | $CF_3$ | — | — | $C(CH_2CH_2)$ | 1-methoxy-cyclo-propyl |
| A.1.62 | Me | $CF_3$ | — | — | $C(CH_2CH_2)$ | 1-hydroxy-cyclo-propyl |
| A.1.63 | Me | $CF_3$ | — | — | $C(CH_2CH_2)$ | 1-trifluoro-methyl-cyclo-propyl |
| A.1.64 | Me | $CF_3$ | — | — | $C(CH_2CH_2)$ | 2-fluoro-cyolo-propyl |
| A.1.65 | Me | $CF_3$ | — | — | $C(CH_2CH_2)$ | 2,2-difluoro-cyclo-propyl |
| A.1.66 | Me | $CF_3$ | — | — | $C(CH_2CH_2)$ | 2-chloro-cyclo-propyl |
| A.1.67 | Me | $CF_3$ | — | — | $C(CH_2CH_2)$ | 2,2-dichloro-cyclo-propyl |
| A.1.68 | Me | $CF_3$ | — | — | $C(CH_2CH_2)$ | 2-bromo-cyclo-propyl |
| A.1.69 | Me | $CF_3$ | — | — | $C(CH_2CH_2)$ | 2,2-dibromo-cyclo-propyl |

TABLE A-continued

Compounds of formula Ia:

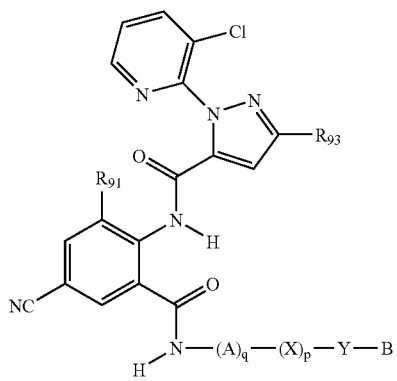

(Ia)

| Comp. No. | R$_{91}$ | R$_{93}$ | A | X | Y | B |
|---|---|---|---|---|---|---|
| A.1.70 | Me | CF$_3$ | — | — | C(CH$_2$CH$_2$) | 2-chloro-2-fluoro-cyclo-propyl |
| A.1.71 | Me | CF$_3$ | — | — | C(CH$_2$CH$_2$) | 2-methyl-cyclo-propyl |
| A.1.72 | Me | CF$_3$ | — | — | C(CH$_2$CH$_2$) | 2,2-dimethyl-cyclo-propyl |
| A.1.73 | Me | CF$_3$ | — | — | C(CH$_2$CH$_2$) | 2-ethyl-cyclo-propyl |
| A.1.74 | Me | CF$_3$ | — | — | C(CH$_2$CH$_2$) | 2,2-diethyl-cyclo-propyl |
| A.1.75 | Me | CF$_3$ | — | — | C(CH$_2$CH$_2$) | 2-cyano-cyclo-propyl |
| A.1.76 | Me | CF$_3$ | — | — | C(CH$_2$CH$_2$) | 2-methyl-thiocyclo-propyl |
| A.1.77 | Me | CF$_3$ | — | — | C(CH$_2$CH$_2$) | 2-methoxy-cyclo-propyl |
| A.1.78 | Me | CF$_3$ | — | — | C(CH$_2$CH$_2$) | 2-hydroxy-cyclo-propyl |
| A.1.79 | Me | CF$_3$ | — | — | C(CH$_2$CH$_2$) | 2-trifluoro-methyl-cyclo-propyl |
| A.1.80 | Me | CF$_3$ | — | — | C(CH$_2$CH$_2$) | cyclo-butyl |
| A.1.81 | Me | CF$_3$ | — | — | C(CH$_2$CH$_2$) | 2-fluoro-cyclo-butyl |
| A.1.82 | Me | CF$_3$ | — | — | C(CH$_2$CH$_2$) | 2,2-difluoro-cyclo-butyl |
| A.1.83 | Me | CF$_3$ | — | — | C(CH$_2$CH$_2$) | 2-chloro-cyclo-butyl |
| A.1.84 | Me | CF$_3$ | — | — | C(CH$_2$CH$_2$) | 2,2-dichloro-cyclo-butyl |
| A.1.85 | Me | CF$_3$ | — | — | C(CH$_2$CH$_2$) | 2-bromo-cyclo-butyl |
| A.1.86 | Me | CF$_3$ | — | — | C(CH$_2$CH$_2$) | 2,2-dibromo-cyclo-butyl |
| A.1.87 | Me | CF$_3$ | — | — | C(CH$_2$CH$_2$) | 2-chloro-2-fluoro-cyclo-butyl |
| A.1.88 | Me | CF$_3$ | — | — | C(CH$_2$CH$_2$) | 2-methyl-cyclo-butyl |
| A.1.89 | Me | CF$_3$ | — | — | C(CH$_2$CH$_2$) | 2,2-dimethyl--cyclo-butyl |
| A.1.90 | Me | CF$_3$ | — | — | C(CH$_2$CH$_2$) | 2-ethyl-cyclo-butyl |
| A.1.91 | Me | CF$_3$ | — | — | C(CH$_2$CH$_2$) | 2,2-diethyl-cyclo-butyl |
| A.1.92 | Me | CF$_3$ | — | — | C(CH$_2$CH$_2$) | 2-cyano-cyclo-butyl |
| A.1.93 | Me | CF$_3$ | — | — | C(CH$_2$CH$_2$) | 2-methyl-thiocyclo-butyl |
| A.1.94 | Me | CF$_3$ | — | — | C(CH$_2$CH$_2$) | 2-methoxy-cyclo-butyl |
| A.1.95 | Me | CF$_3$ | — | — | C(CH$_2$CH$_2$) | 2-hydroxy-cyclo-butyl |
| A.1.96 | Me | CF$_3$ | — | — | C(CH$_2$CH$_2$) | 2-trifluoro-methyl-cyclo-butyl |
| A.1.97 | Me | CF$_3$ | — | — | C(CH$_2$CH$_2$) | 3-methyl-cyclo-butyl |
| A.1.98 | Me | CF$_3$ | — | — | C(CH$_2$CH$_2$) | 3,3-dimethyl--cyclo-butyl |
| A.1.99 | Me | CF$_3$ | — | — | C(CH$_2$CH$_2$) | 3-chloro-cyclo-butyl |
| A.1.100 | Me | CF$_3$ | — | — | C(CH$_2$CH$_2$) | 3,3-dichloro-cyclo-butyl |
| A.1.101 | Me | CF$_3$ | — | — | C(CH$_2$CH$_2$) | CH(CH$_2$O) |
| A.1.102 | Me | CF$_3$ | — | — | C(CH$_2$CH$_2$) | CH(CH-MeO) |
| A.1.103 | Me | CF$_3$ | — | — | C(CH$_2$CH$_2$) | CH(C-Me$_2$O) |

TABLE A-continued

Compounds of formula Ia:

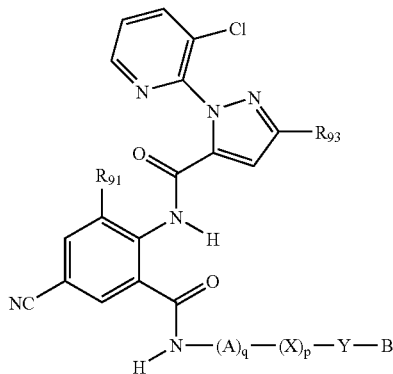

(Ia)

| Comp. No. | $R_{91}$ | $R_{93}$ | A | X | Y | B |
|---|---|---|---|---|---|---|
| A.1.104 | Me | $CF_3$ | — | — | $C(CH_2CH_2)$ | $CH(CH_2S)$ |
| A.1.105 | Me | $CF_3$ | — | — | $C(CH_2CH_2)$ | $CH(CH_2OCH_2)$ |
| A.1.106 | Me | $CF_3$ | — | — | $C(CH_2CH_2)$ | $CH(CHMeOCH_2)$ |
| A.1.107 | Me | $CF_3$ | — | — | $C(CH_2CH_2)$ | $CH(CMe_2OCH_2)$ |
| A.1.108 | Me | $CF_3$ | — | — | $C(CH_2CH_2)$ | $CH(CH_2-S(O)_2CH_2)$ |
| A.1.109 | Me | $CF_3$ | — | — | $C(CH_2CH_2)$ | $CH(CHMeS(O)_2CH_2)$ |
| A.1.110 | Me | $CF_3$ | — | — | $C(CH_2CH_2)$ | $CH(CMe_2S(O)_2CH_2)$ |
| A.1.111 | Me | $CF_3$ | — | — | $C(CH_2CH_2)$ | $C(Me)-(CH_2O)$ |
| A.1.112 | Me | $CF_3$ | — | — | $C(CH_2CH_2)$ | $C(Me)-(CHMeO)$ |
| A.1.113 | Me | $CF_3$ | — | — | $C(CH_2CH_2)$ | $C(Me)-(CMe_2O)$ |
| A.1.114 | Me | $CF_3$ | — | — | $C(CH_2CH_2)$ | $C(Me)-(CH_2S)$ |
| A.1.115 | Me | $CF_3$ | — | — | $C(CH_2CH_2)$ | $C(Me)-(CH_2OCH_2)$ |
| A.1.116 | Me | $CF_3$ | — | — | $C(CH_2CH_2)$ | $C(Me)-(CHMeO-CH_2)$ |
| A.1.117 | Me | $CF_3$ | — | — | $C(CH_2CH_2)$ | $C(Me)-(C-Me_2OCH_2)$ |
| A.1.118 | Me | $CF_3$ | — | — | $C(CH_2CH_2)$ | $C(Me)-(CH_2S(O)_2CH_2)$ |
| A.1.119 | Me | $CF_3$ | — | — | $C(CH_2CH_2)$ | $C(Me)-(CH-MeS(O)_2CH_2)$ |
| A.1.120 | Me | $CF_3$ | — | — | $C(CH_2CH_2)$ | $CMe(C-Me_2S(O)_2CH_2)$ |
| A.1.121 | Me | $CF_3$ | — | — | $C(CH_2CH_2)$ | 1-(COOEt)-cyclo-propyl |
| A.1.122 | Me | SMe | — | — | $C(CH_2CH_2)$ | cyclo-propyl |
| A.1.123 | Cl | SMe | — | — | $C(CH_2CH_2)$ | cyclo-propyl |
| A.1.124 | Br | SMe | — | — | $C(CH_2CH_2)$ | cyclo-propyl |
| A.1.125 | Me | SOMe | — | — | $C(CH_2CH_2)$ | cyclo-propyl |
| A.1.126 | Cl | SOMe | — | — | $C(CH_2CH_2)$ | cyclo-propyl |
| A.1.127 | Br | SOMe | — | — | $C(CH_2CH_2)$ | cyclo-propyl |
| A.1.128 | Me | $SO_2Me$ | — | — | $C(CH_2CH_2)$ | cyclo-propyl |
| A.1.129 | Cl | $SO_2Me$ | — | — | $C(CH_2CH_2)$ | cyclo-propyl |
| A.1.130 | Br | $SO_2Me$ | — | — | $C(CH_2CH_2)$ | cyclo-propyl |
| A.1.131 | Me | $OCF_2CFHCF_3$ | — | — | $C(CH_2CH_2)$ | cyclo-propyl |
| A.1.132 | Cl | $OCF_2CFHCF_3$ | — | — | $C(CH_2CH_2)$ | cyclo-propyl |
| A.1.133 | Br | $OCF_2CFHCF_3$ | — | — | $C(CH_2CH_2)$ | cyclo-propyl |
| A.1.134 | Me | $OCH_2CF_2CF_3$ | — | — | $C(CH_2CH_2)$ | cyclo-propyl |
| A.1.135 | Cl | $OCH_2CF_2CF_3$ | — | — | $C(CH_2CH_2)$ | cyclo-propyl |
| A.1.136 | Br | $OCH_2CF_2CF_3$ | — | — | $C(CH_2CH_2)$ | cyclo-propyl |

TABLE B

Compounds of formula Ib:

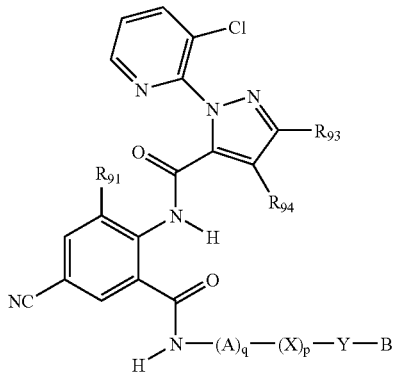

(Ib)

| Comp. No. | R$_{91}$ | R$_{93}$ | R$_{94}$ | A | X | Y | B |
|---|---|---|---|---|---|---|---|
| B.1.1 | Me | CF$_3$ | Br | — | — | C(CH$_2$CH$_2$) | cyclo-propyl |
| B.1.2 | Cl | CF$_3$ | Br | — | — | C(CH$_2$CH$_2$) | cyclo-propyl |
| B.1.3 | Br | CF$_3$ | Br | — | — | C(CH$_2$CH$_2$) | cyclo-propyl |
| B.1.4 | Me | Cl | Br | — | — | C(CH$_2$CH$_2$) | cyclo-propyl |
| B.1.5 | Cl | Cl | Br | — | — | C(CH$_2$CH$_2$) | cyclo-propyl |
| B.1.6 | Br | Cl | Br | — | — | C(CH$_2$CH$_2$) | cyclo-propyl |
| B.1.7 | Me | Br | Br | — | — | C(CH$_2$CH$_2$) | cyclo-propyl |
| B.1.8 | Cl | Br | Br | — | — | C(CH$_2$CH$_2$) | cyclo-propyl |
| B.1.9 | Br | Br | Br | — | — | C(CH$_2$CH$_2$) | cyclo-propyl |
| B.1.10 | Me | CF$_3$ | Cl | — | — | C(CH$_2$CH$_2$) | cyclo-propyl |
| B.1.11 | Cl | CF$_3$ | Cl | — | — | C(CH$_2$CH$_2$) | cyclo-propyl |
| B.1.12 | Br | CF$_3$ | Cl | — | — | C(CH$_2$CH$_2$) | cyclo-propyl |
| B.1.13 | Me | Cl | Cl | — | — | C(CH$_2$CH$_2$) | cyclo-propyl |
| B.1.14 | Cl | Cl | Cl | — | — | C(CH$_2$CH$_2$) | cyclo-propyl |
| B.1.15 | Br | Cl | Cl | — | — | C(CH$_2$CH$_2$) | cyclo-propyl |
| B.1.16 | Me | Br | Cl | — | — | C(CH$_2$CH$_2$) | cyclo-propyl |
| B.1.17 | Cl | Br | Cl | — | — | C(CH$_2$CH$_2$) | cyclo-propyl |
| B.1.18 | Br | Br | Cl | — | — | C(CH$_2$CH$_2$) | cyclo-propyl |
| B.1.19 | Me | CF$_3$ | Me | — | — | C(CH$_2$CH$_2$) | cyclo-propyl |
| B.1.20 | Cl | CF$_3$ | Me | — | — | C(CH$_2$CH$_2$) | cyclo-propyl |
| B.1.21 | Br | CF$_3$ | Me | — | — | C(CH$_2$CH$_2$) | cyclo-propyl |
| B.1.22 | Me | Cl | Me | — | — | C(CH$_2$CH$_2$) | cyclo-propyl |
| B.1.23 | Cl | Cl | Me | — | — | C(CH$_2$CH$_2$) | cyclo-propyl |
| B.1.24 | Br | Cl | Me | — | — | C(CH$_2$CH$_2$) | cyclo-propyl |
| B.1.25 | Me | Br | Me | — | — | C(CH$_2$CH$_2$) | cyclo-propyl |
| B.1.26 | Cl | Br | Me | — | — | C(CH$_2$CH$_2$) | cyclo-propyl |
| B.1.27 | Br | Br | Me | — | — | C(CH$_2$CH$_2$) | cyclo-propyl |
| B.1.28 | Me | OCH$_2$CF$_3$ | Br | — | — | C(CH$_2$CH$_2$) | cyclo-propyl |
| B.1.29 | Cl | OCH$_2$CF$_3$ | Br | — | — | C(CH$_2$CH$_2$) | cyclo-propyl |
| B.1.30 | Br | OCH$_2$CF$_3$ | Br | — | — | C(CH$_2$CH$_2$) | cyclo-propyl |
| B.1.31 | Me | OCH$_2$CF$_3$ | Cl | — | — | C(CH$_2$CH$_2$) | cyclo-propyl |
| B.1.32 | Cl | OCH$_2$CF$_3$ | Cl | — | — | C(CH$_2$CH$_2$) | cyclo-propyl |
| B.1.33 | Br | OCH$_2$CF$_3$ | Cl | — | — | C(CH$_2$CH$_2$) | cyclo-propyl |
| B.1.34 | Me | OCH$_2$CF$_3$ | Me | — | — | C(CH$_2$CH$_2$) | cyclo-propyl |
| B.1.35 | Cl | OCH$_2$CF$_3$ | Me | — | — | C(CH$_2$CH$_2$) | cyclo-propyl |
| B.1.36 | Br | OCH$_2$CF$_3$ | Me | — | — | C(CH$_2$CH$_2$) | cyclo-propyl |

TABLE C

Physical data of the compounds of table A and B:

| Compound No. | m.p. [° C.] |
|---|---|
| A.1.1 | 270-272 |
| A.1.13 | 175-178 |
| A.1.4 | 249-255 |
| A.1.7 | 254-260 |
| B.1.28 | 169-174 |
| A.1.122 | 243-244 |
| A.1.131 | 170-172 |
| A.1.134 | 200-205 |
| A.1.16 | 250-251 |
| A.1.72 | 158-160 |
| A.1.57 | 247-249 |

TABLE D

Compounds of formula Va:

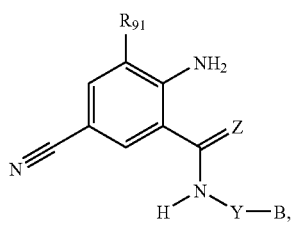

(Va)

| Comp. No. | R$_{91}$ | Y | B | m.p. [° C.] |
|---|---|---|---|---|
| D1 | Me | C(CH$_2$CH$_2$) | cyclo-propyl | 171-172 |
| D2 | Me | CH(cyclo-propyl) | cyclo-propyl | |
| D3 | Me | C(CH$_2$CHF) | cyclo-propyl | |
| D4 | Me | C(CH$_2$CF$_2$) | cyclo-propyl | |

TABLE D-continued

Compounds of formula Va:

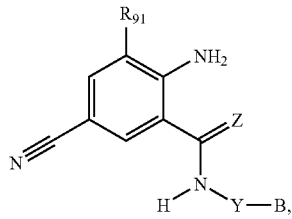

(Va)

| Comp. No. | $R_{91}$ | Y | B | m.p. [° C.] |
|---|---|---|---|---|
| D4 | Me | C(CH$_2$CHCl) | cyclo-propyl | |
| D6 | Me | C(CH$_2$CFCl) | cyclo-propyl | |
| D7 | Me | C(CH$_2$CCl$_2$) | cyclo-propyl | |
| D8 | Me | C(CH$_2$CHBr) | cyclo-propyl | |
| D9 | Me | C(CH$_2$CBr$_2$) | cyclo-propyl | |
| D11 | Me | C(CH$_2$CMe$_2$) | cyclo-propyl | |
| D12 | Me | C(CH$_2$CHEt) | cyclo-propyl | |
| D13 | Me | C(CH$_2$CEt$_2$) | cyclo-propyl | |
| D14 | Me | C(CH$_2$OCH$_2$) | cyclo-propyl | |
| D15 | Me | C(CH$_2$S(O)$_2$—CH$_2$ | cyclo-propyl | |
| D16 | Me | C(CH$_2$CH$_2$) | 1-fluoro-cyclo-propyl | |
| D17 | Me | C(CH$_2$CH$_2$) | 1-chloro-cyclo-propyl | |
| D18 | Me | C(CH$_2$CH$_2$) | 1-bromo-cyclo-propyl | |
| D19 | Me | C(CH$_2$CH$_2$) | 1-methyl--cyclo-propyl | |
| D20 | Me | C(CH$_2$CH$_2$) | 1-ethyl-cyclo-propyl | |
| D21 | Me | C(CH$_2$CH$_2$) | 1-cyano-cyclo-propyl | |
| D22 | Me | C(CH$_2$CH$_2$) | 1-methyl--thiocyclo-propyl | |
| D23 | Me | C(CH$_2$CH$_2$) | 1-methoxy-cyclo-propyl | |
| D24 | Me | C(CH$_2$CH$_2$) | 1-hydroxy-cyclo-propyl | |
| D25 | Me | C(CH$_2$CH$_2$) | 1-trifluoro-methyl-cyclo-propyl | |
| D26 | Me | C(CH$_2$CH$_2$) | 2-fluoro-cyclo-propyl | |
| D27 | Me | C(CH$_2$CH$_2$) | 2,2-difluoro-cyclo-propyl | |
| D28 | Me | C(CH$_2$CH$_2$) | 2-chloro-cyclo-propyl | |
| D29 | Me | C(CH$_2$CH$_2$) | 2,2-dichloro-cyclo-propyl | |
| D30 | Me | C(CH$_2$CH$_2$) | 2-bromo-cyclo-propyl | |
| D31 | Me | C(CH$_2$CH$_2$) | 2,2-dibromo-cyclo-propyl | |
| D32 | Me | C(CH$_2$CH$_2$) | 2-chloro-2-fluoro-cyclo-propyl | |
| D33 | Me | C(CH$_2$CH$_2$) | 2-methyl-cyclo-propyl | |
| D34 | Me | C(CH$_2$CH$_2$) | 2,2-dimethyl-cyclo-propyl | |
| D35 | Me | C(CH$_2$CH$_2$) | 2-ethyl-cyclo-propyl | |
| D36 | Me | C(CH$_2$CH$_2$) | 2,2-diethyl-cyclo-propyl | |
| D37 | Me | C(CH$_2$CH$_2$) | 2-cyano-cyclo-propyl | |
| D38 | Me | C(CH$_2$CH$_2$) | 2-methyl-thiocyclo-propyl | |
| D39 | Me | C(CH$_2$CH$_2$) | 2-methoxy-cyclo-propyl | |
| D40 | Me | C(CH$_2$CH$_2$) | 2-hydroxy-cyclo-propyl | |
| D41 | Me | C(CH$_2$CH$_2$) | 2-trifluoro-methyl-cyclo-propyl | |
| D42 | Me | C(CH$_2$CH$_2$) | cyclo-butyl | |
| D43 | Me | C(CH$_2$CH$_2$) | 2-fluoro-cyclo-butyl | |
| D44 | Me | C(CH$_2$CH$_2$) | 2,2-difluoro-cyclo-butyl | |
| D45 | Me | C(CH$_2$CH$_2$) | 2-chloro-cyclo-butyl | |
| D46 | Me | C(CH$_2$CH$_2$) | 2,2-dichloro-cyclo-butyl | |
| D47 | Me | C(CH$_2$CH$_2$) | 2-bromo-cyclo-butyl | |
| D48 | Me | C(CH$_2$CH$_2$) | 2,2-dibromo-cyclo-butyl | |
| D49 | Me | C(CH$_2$CH$_2$) | 2-chloro-2-fluoro-cyclo-butyl | |
| D50 | Me | C(CH$_2$CH$_2$) | 2-methyl-cyclo-butyl | |
| D51 | Me | C(CH$_2$CH$_2$) | 2,2-dimethyl--cyclo-butyl | |
| D52 | Me | C(CH$_2$CH$_2$) | 2-ethyl-cyclo-butyl | |
| D53 | Me | C(CH$_2$CH$_2$) | 2,2-diethyl-cyclo-butyl | |
| D54 | Me | C(CH$_2$CH$_2$) | 2-cyano-cyclo-butyl | |
| D55 | Me | C(CH$_2$CH$_2$) | 2-methyl-thiocyclo-butyl | |
| D56 | Me | C(CH$_2$CH$_2$) | 2-methoxy-cyclo-butyl | |
| D57 | Me | C(CH$_2$CH$_2$) | 2-hydroxy-cyclo-butyl | |
| D58 | Me | C(CH$_2$CH$_2$) | 2-trifluoro-methyl-cyclo-butyl | |
| D59 | Me | C(CH$_2$CH$_2$) | 3-methyl-cyclo-butyl | |
| D60 | Me | C(CH$_2$CH$_2$) | 3,3-dimethyl--cyclo-butyl | |
| D61 | Me | C(CH$_2$CH$_2$) | 3-chloro-cyclo-butyl | |
| D62 | Me | C(CH$_2$CH$_2$) | 3,3-dichloro-cyclo-butyl | |
| D63 | Me | C(CH$_2$CH$_2$) | CH(CH$_2$O) | |
| D64 | Me | C(CH$_2$CH$_2$) | CH(CH-MeO) | |
| D65 | Me | C(CH$_2$CH$_2$) | CH(C-Me$_2$O) | |
| D66 | Me | C(CH$_2$CH$_2$) | CH(CH$_2$S) | |
| D67 | Me | C(CH$_2$CH$_2$) | CH(CH$_2$OCH$_2$) | |

TABLE D-continued

Compounds of formula Va:

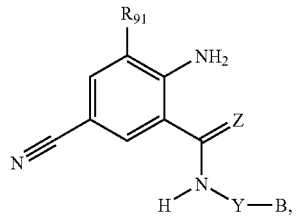

(Va)

| Comp. No. | $R_{91}$ | Y | B | m.p. [° C.] |
|---|---|---|---|---|
| D68 | Me | C(CH$_2$CH$_2$) | CH(CHMeOCH$_2$) | |
| D69 | Me | C(CH$_2$CH$_2$) | CH(CMe$_2$OCH$_2$) | |
| D70 | Me | C(CH$_2$CH$_2$) | CH(CH$_2$—S(O)$_2$CH$_2$) | |
| D71 | Me | C(CH$_2$CH$_2$) | CH(CHMeS(O)$_2$CH$_2$) | |
| D72 | Me | C(CH$_2$CH$_2$) | CH(CMe$_2$S(O)$_2$CH$_2$) | |
| D73 | Me | C(CH$_2$CH$_2$) | C(Me)-(CH$_2$O) | |
| D74 | Me | C(CH$_2$CH$_2$) | C(Me)-(CHMeO) | |
| D75 | Me | C(CH$_2$CH$_2$) | C(Me)-(CMe$_2$O) | |
| D76 | Me | C(CH$_2$CH$_2$) | C(Me)-(CH$_2$S) | |
| D77 | Me | C(CH$_2$CH$_2$) | C(Me)-(CH$_2$OCH$_2$) | |
| D78 | Me | C(CH$_2$CH$_2$) | C(Me)-(CHMeO-CH$_2$) | |
| D79 | Me | C(CH$_2$CH$_2$) | C(Me)-(C-Me$_2$OCH$_2$) | |
| D80 | Me | C(CH$_2$CH$_2$) | C(Me)-(CH$_2$S(O)$_2$CH$_2$) | |
| D81 | Me | C(CH$_2$CH$_2$) | C(Me)-(CH-MeS(O)$_2$CH$_2$) | |
| D82 | Me | C(CH$_2$CH$_2$) | CMe(C-Me$_2$S(O)$_2$CH$_2$) | |
| D83 | Me | C(CH$_2$CH$_2$) | 1-(COOEt)-cyclo-propyl | |
| D84 | Cl | C(CH$_2$CH$_2$) | cyclo-propyl | |
| D85 | Br | C(CH$_2$CH$_2$) | cyclo-propyl | |
| D86 | Cl | C(CH$_2$CH$_2$) | 1-methyl-cyclo-propyl | |
| D87 | Br | C(CH$_2$CH$_2$) | 1-methyl-cyclo-propyl | |
| D88 | Cl | C(CH$_2$CH$_2$) | 2,2-dimethyl-cyclo-propyl | |
| D89 | Br | C(CH$_2$CH$_2$) | 2,2-dimethyl-cyclo-propyl | |

Formulation examples (%=percent by weight)

EXAMPLE F1

Emulsion concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

EXAMPLE F2

Solutions

| | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

EXAMPLE F3

Granules

| | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

EXAMPLE F4

Dusts

| | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

EXAMPLE F5

Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

EXAMPLE F6

Extruder granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

EXAMPLE F7

Coated granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

EXAMPLE F8

Suspension concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compounds according to the invention can be broadened considerably, and adapted to prevailing circumstances, by adding other insecticidally or acaricidally active ingredients. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds specifically described in tables A and B of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chlorpropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1 157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT(219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyridifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyidithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanli* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E+TX, Z)-tetradeca-4+TX, 10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E+TX, 9Z)-dodeca-7+TX, 9-dien-1-yl acetate (IUPAC name) (283)+TX, (9Z+TX, 11E)-tetradeca-9+TX, 11-dien-1-yl acetate (IUPAC name) (780)+TX, (9Z+TX, 12E)-tetradeca-9+TX, 12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, mediure [CCN]+TX, megatomoic acid (alternative name) [CCN]+TX, methyl eugenol (alternative name) (540)+TX, muscalure (563)+TX, octadeca-2+TX, 13-dien-1-yl acetate (IUPAC name) (588)+TX, octadeca-3 +TX, 13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1+TX, 1-dichloro-1-nitroethane (IUPAC/Chemical Abstracts name) (1058)+TX, 1+TX, 1-dichloro-2+TX, 2-bis(4-ethylphenyl)ethane (IUPAC name) (1056)+TX, 1+TX, 2-dichloropropane (IUPAC/Chemical Abstracts name) (1062)+TX, 1+TX, 2-dichloropropane with 1+TX, 3-dichloropropene (IUPAC name) (1063)+TX, 1-bromo-2-chloroethane (IUPAC/Chemical Abstracts name) (916)+TX, 2+TX, 2+TX, 2-trichloro-1-(3 +TX, 4-dichlorophenyl)ethyl acetate (IUPAC name) (1451)+TX, 2+TX, 2-dichlorovinyl 2-ethylsulfinylethyl methyl phosphate (IUPAC name) (1066)+TX, 2-(1+TX, 3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4+TX, 5-dimethyl-1+TX, 3-dioxolan-2-yl)phenyl methylcarbamate (IUPAC/Chemical Abstracts name) (1084)+TX, 2-(4-chloro-3+TX, 5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1+TX, 3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3+TX, 5-xylyl methylcarbamate (IUPAC name) (1285)+TX, 5+TX, 5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethyinon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472) +TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metoicarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, niflurdide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1+TX, 2-dibromo-3-chloropropane (IUPAC/Chemical Abstracts name) (1045)+TX, 1+TX, 2-dichloropropane (IUPAC/Chemical Abstracts name) (1062)+TX, 1+TX, 2-dichloropropane with 1+TX, 3-dichloropropene (IUPAC name) (1063)+TX, 1+TX, 3-dichloropropene (233)+TX, 3+TX, 4-dichlorotetrahydrothiophene 1+TX, 1-dioxide (IUPAC/Chemical Abstracts name) (1065)+TX, 3-(4-chlorophenyl)-5-methylrhodanine (IUPAC name) (980)+TX, 5-methyl-6-thioxo-1+TX, 3+TX, 5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1+TX, 3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1+TX, 3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, and a wound protectant selected from the group of substances consisting of mercuric oxide (512)+TX, octhilinone (590) and thiophanate-methyl (802)+TX, the compound of Formula A-1

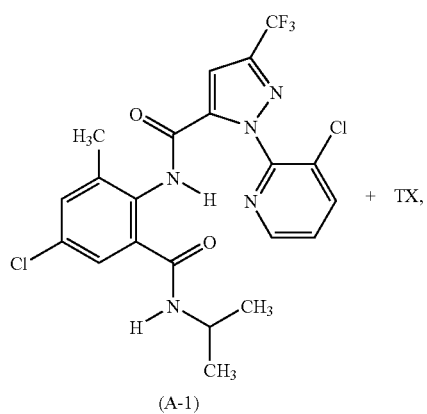

(A-1)

the formula A-2

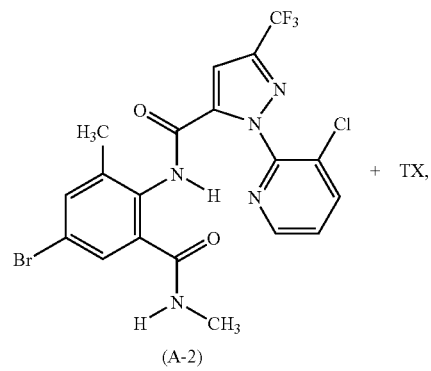

(A-2)

the formula A-3

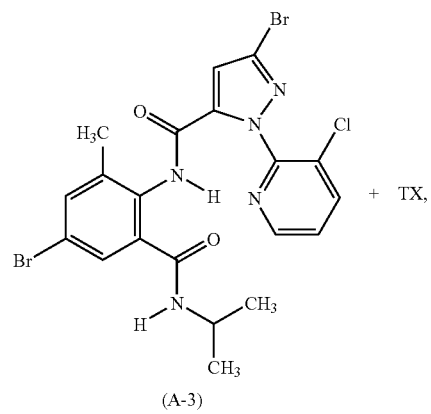

(A-3)

the formula A-4

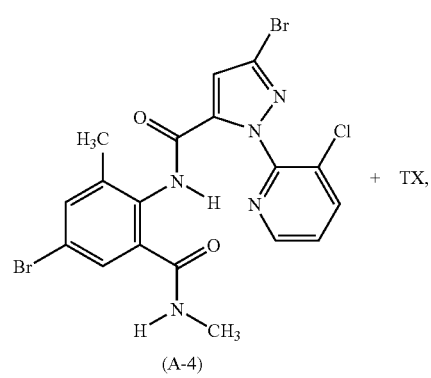

(A-4)

the formula A-5
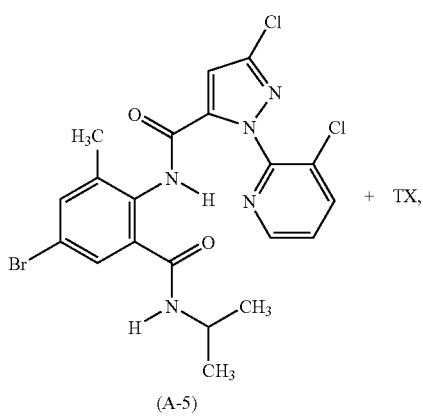
(A-5)   + TX,
the formula A-6
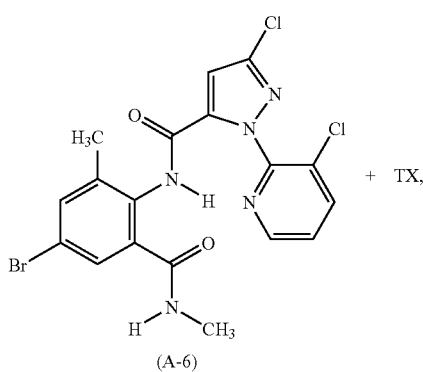
(A-6)   + TX,
the formula A-7
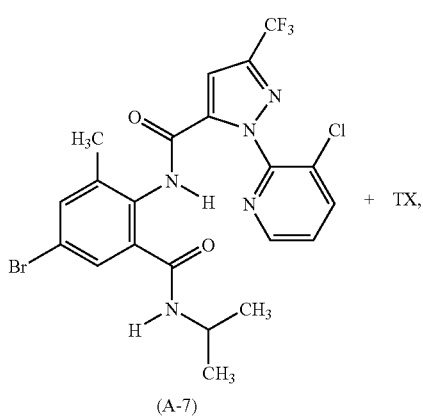
(A-7)   + TX,
the formula A-8
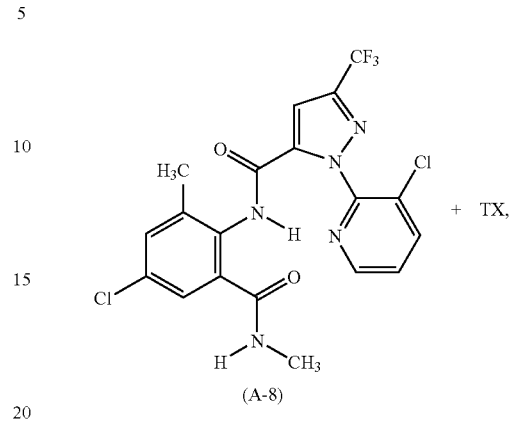
(A-8)   + TX,
the formula A-9
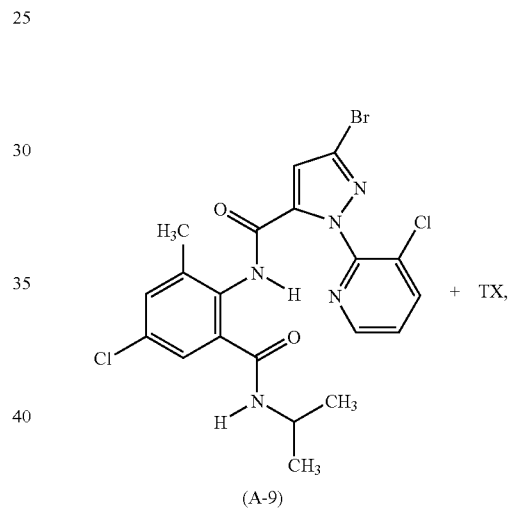
(A-9)   + TX,
the formula A-10
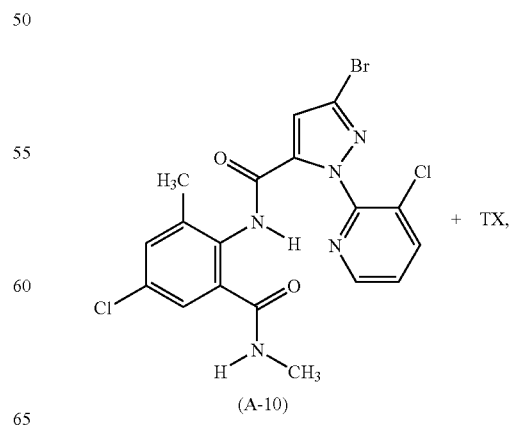
(A-10)   + TX, the formula A-11
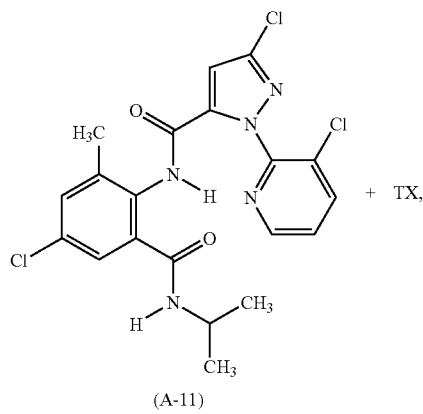
(A-11) + TX,
the formula A-12
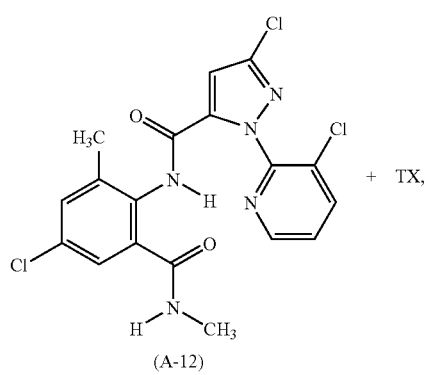
(A-12) + TX,
the formula A-13
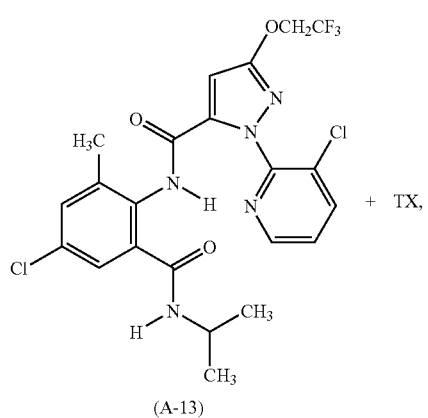
(A-13) + TX,
the formula A-14
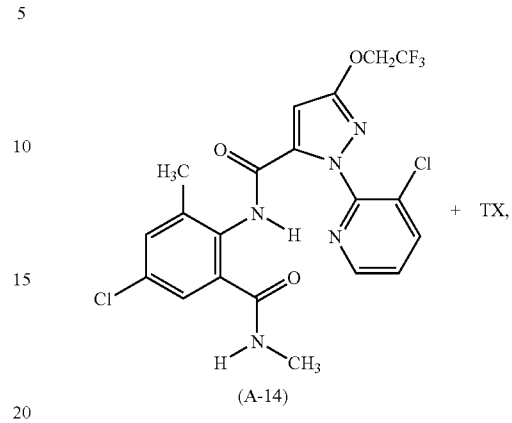
(A-14) + TX,
the formula A-15
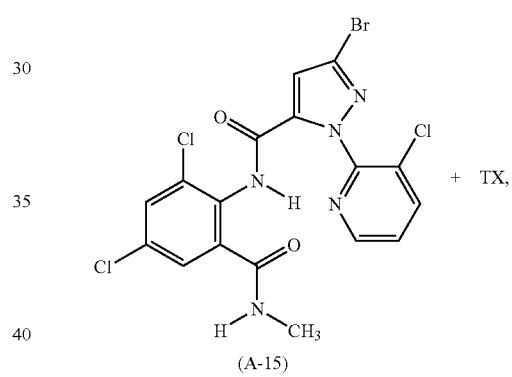
(A-15) + TX,
the formula A-16
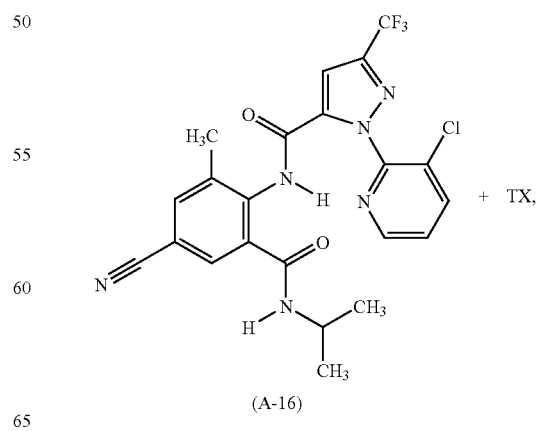
(A-16) + TX, the formula A-17
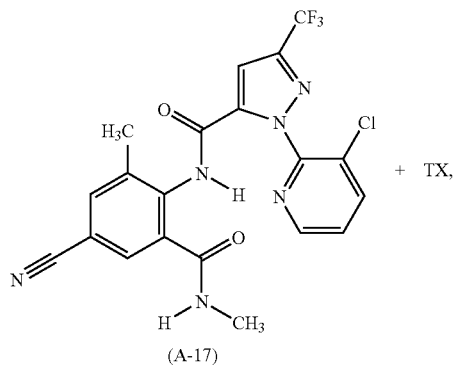
(A-17)
the formula A-18
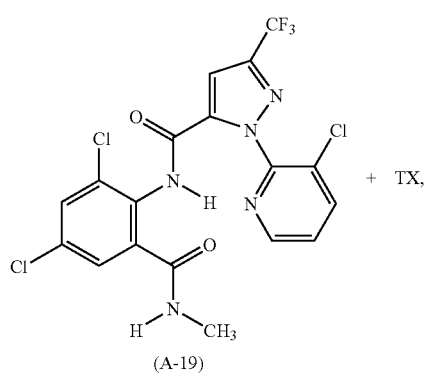
(A-18)
the formula A-19
the formula A-20
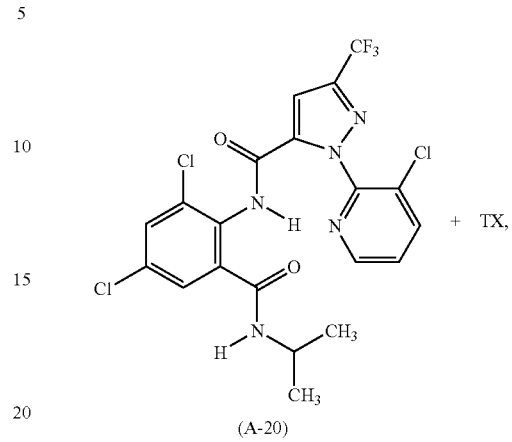
(A-20)
the formula A-21
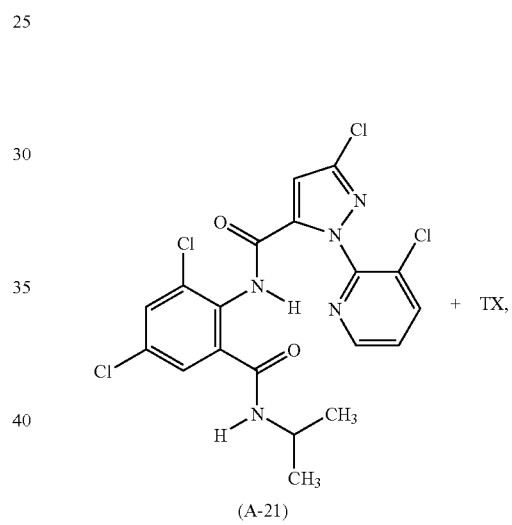
(A-21)
the formula A-22 the formula A-23

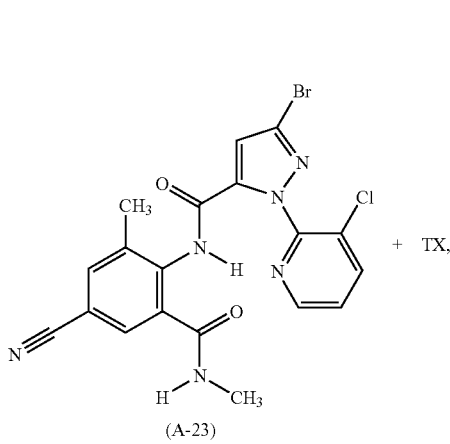

(A-23) + TX, the formula A-24

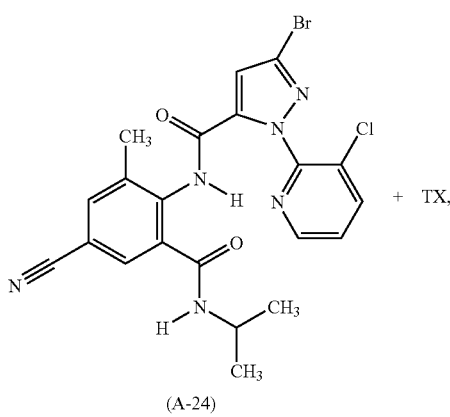

(A-24) + TX, the formula A-25

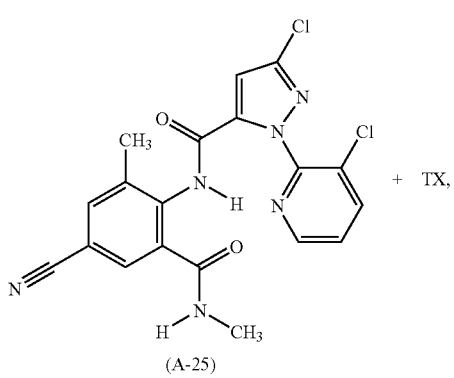

(A-25) + TX, the formula A-26

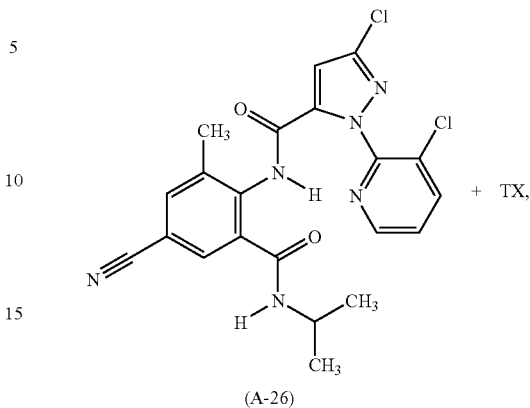

(A-26) + TX, and Azaconazole (60207-31-0]+TX, Bitertanol [70585-36-3]+TX, Bromuconazole [116255-48-2]+TX, Cyproconazole [94361-06-5]+TX, Difenoconazole [119446-68-3]+TX, Diniconazole [83657-24-3]+TX, Epoxiconazole [106325-08-0]+TX, Fenbuconazole [114369-43-6]+TX, Fluquinconazole [136426-54-5]+TX, Flusilazole [85509-19-9]+TX, Flutriafol [76674-21-0]+TX, Hexaconazole [79983-71-4]+TX, Imazalil [35554-44-0]+TX, Imibenconazole [86598-92-7]+TX, Ipconazole [125225-28-7]+TX, Metconazole [125116-23-6]+TX, Myclobutanil [88671-89-0]+TX, Pefurazoate [101903-30-4]+TX, Penconazole [66246-88-6]+TX, Prothioconazole [178928-70-6]+TX, Pyrifenox [88283-41-4]+TX, Prochloraz [67747-09-5]+TX, Propiconazole [60207-90-1]+TX, Simeconazole [149508-90-7]+TX, Tebuconazole [107534-96-3]+TX, Tetraconazole [112281-77-3]+TX, Triadimefon [43121-43-3]+TX, Triadimenol [55219-65-3]+TX, Triflumizole [99387-89-0]+TX, Triticonazole [131983-72-7]+TX, Ancymidol [12771-68-5]+TX, Fenarimol [60168-88-9]+TX, Nuarimol [63284-71-9]+TX, Bupirimate [41483-43-6]+TX, Dimethirimol [5221-53-4]+TX, Ethirimol [23947-60-6]+TX, Dodemorph [1593-77-7]+TX, Fenpropidine [67306-00-7]+TX, Fenpropimorph [67564-91-4]+TX, Spiroxamine [118134-30-8]+TX, Tridemorph [81412-43-3]+TX, Cyprodinil [121552-61-2]+TX, Mepanipyrim [110235-47-7]+TX, Pyrimethanil [53112-28-0]+TX, Fenpiclonil [74738-17-3]+TX, Fludioxonil [131341-86-1]+TX, Benalaxyl [71626-11-4]+TX, Furalaxyl[57646-30-7]+TX, Metalaxyl [57837-19-1]+TX, R-Metalaxyl [70630-17-0]+TX, Ofurace [58810-48-3]+TX, Oxadixyl [77732-09-3]+TX, Benomyl [17804-35-2]+TX, Carbendazim [10605-21-7]+TX, Debacarb [62732-91-6]+TX, Fuberidazole [3878-19-1]+TX, Thiabendazole [148-79-8]+TX, Chlozolinate [84332-86-5]+TX, Dichlozoline [24201-58-9]+TX, Iprodione [36734-19-7]+TX, Myclozoline [54864-61-8]+TX, Procymidone [32809-16-8]+TX, Vinclozoline [50471-44-8]+TX, Boscalid [188425-85-6]+TX, Carboxin [5234-68-4]+TX, Fenfuram [24691-80-3]+TX, Flutolanil [66332-96-5]+TX, Mepronil [55814-41-0]+TX, Oxycarboxin [5259-88-1]+TX, Penthiopyrad [183675-82-3]+TX, Thifluzamide [130000-40-7]+TX, Guazatine [108173-90-6]+TX, Dodine [2439-10-3][112-65-2] (freie Base)+TX, Iminoctadine [13516-27-3]+TX, Azoxystrobin [131860-33-8]+TX, Dimoxystrobin [149961-52-4]+TX, Enestroburin {Proc. BCPC+TX, Int. Congr.+TX, Glasgow+TX, 2003+TX, 1+TX, 93}+TX, Fluoxastrobin [361377-29-9]+TX, Kresoxim-methyl [143390-89-0]+TX, Metominostrobin [133408-50-1]+TX, Trifloxystrobin [141517-21-7]+

TX, Orysastrobin [248593-16-0]+TX, Picoxystrobin [117428-22-5]+TX, Pyraclostrobin [175013-18-0]+TX, Ferbam [14484-64-1]+TX, Mancozeb [8018-01-7]+TX, Maneb [12427-38-2]+TX, Metiram [9006-42-2]+TX, Propineb [12071-83-9]+TX, Thiram [137-26-8]+TX, Zineb [12122-67-7]+TX, Ziram [137-30-4]+TX, Captafol [2425-06-1]+TX, Captan [133-06-2]+TX, Dichlofluanid [1085-98-9]+TX, Fluoroimide [41205-21-4]+TX, Folpet [133-07-3]+TX, Tolylfluanid [731-27-1]+TX, Bordeaux Mixture [8011-63-0]+TX, Copperhydroxid [20427-59-2]+TX, Copperoxychlorid [1332-40-7]+TX, Coppersulfat [7758-98-7]+TX, Copperoxid [1317-39-1]+TX, Mancopper [53988-93-5]+TX, Oxine-copper [10380-28-6]+TX, Dinocap [131-72-6]+TX, Nitrothal-isopropyl [10552-74-6]+TX, Edifenphos [17109-49-8]+TX, Iprobenphos [26087-47-8]+TX, Isoprothiolane [50512-35-1]+TX, Phosdiphen [36519-00-3]+TX, Pyrazophos [13457-18-6]+TX, Tolclofos-methyl [57018-04-9]+TX, Acibenzolar-S-methyl [135158-54-2]+TX, Anilazine [101-05-3]+TX, Benthiavalicarb [413615-35-7]+TX, Blasticidin-S [2079-00-7]+TX, Chinomethionat [2439-01-2]+TX, Chloroneb [2675-77-6]+TX, Chlorothalonil [1897-45-6]+TX, Cyflufenamid [180409-60-3]+TX, Cymoxanil [57966-95-7]+TX, Dichlone [117-80-6]+TX, Diclocymet [139920-32-4]+TX, Diclomezine [62865-36-5]+TX, Dicloran [99-30-9]+TX, Diethofencarb [87130-20-9]+TX, Dimethomorph [110488-70-5]+TX, SYP-LI90 (Flumorph) [211867-47-9]+TX, Dithianon [3347-22-6]+TX, Ethaboxam [162650-77-3]+TX, Etridiazole [2593-15-9]+TX, Famoxadone [131807-57-3]+TX, Fenamidone [161326-34-7]+TX, Fenoxanil [115852-48-7]+TX, Fentin [668-34-8]+TX, Ferimzone [89269-64-7]+TX, Fluazinam [79622-59-6]+TX, Fluopicolide [239110-15-7]+TX, Flusulfamide [106917-52-6]+TX, Fenhexamid [126833-17-8]+TX, Fosetyl-aluminium [39148-24-8]+TX, Hymexazol [10004-44-1]+TX, Iprovalicarb [140923-17-7]+TX, IKF-916 (Cyazofamid) [120116-88-3]+TX, Kasugamycin [6980-18-3]+TX, Methasulfocarb [66952-49-6]+TX, Metrafenone [220899-03-6]+TX, Pencycuron [66063-05-6]+TX, Phthalide [27355-22-2]+TX, Polyoxins [11113-80-7]+TX, Probenazole [27605-76-1]+TX, Propamocarb [25606-41-1]+TX, Proquinazid [189278-12-4]+TX, Pyroquilon [57369-32-1]+TX, Quinoxyfen [124495-18-7]+TX, Quintozene [82-68-8]+TX, Schwefel [7704-34-9]+TX, Tiadinil [223580-51-6]+TX, Triazoxide [72459-58-6]+TX, Tricyclazole [41814-78-2]+TX, Triforine [26644-46-2]+TX, Validamycin [37248-47-8]+TX, Zoxamide (RH7281) [156052-68-5]+TX, Mandipropamid [374726-62-2]+TX, the compound of formula F-1

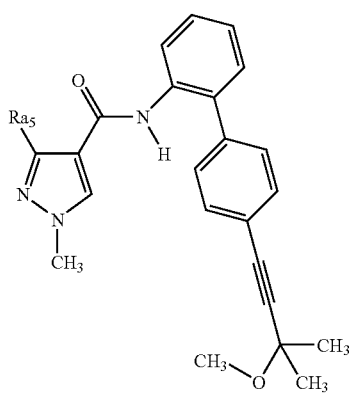

(F-1)

wherein $Ra_5$ is trifluoromethyl or difluoromethyl (WO2004/058723)+TX, the compound of formula F-2

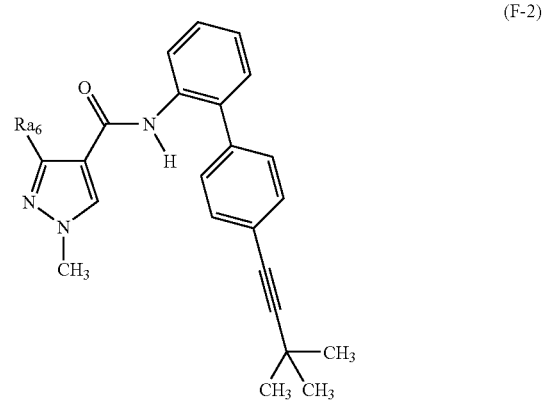

(F-2)

wherein $Ra_6$ is trifluoromethyl or difluoromethyl (WO2004/058723)+TX, the racemic compound of formula F-3 (syn)

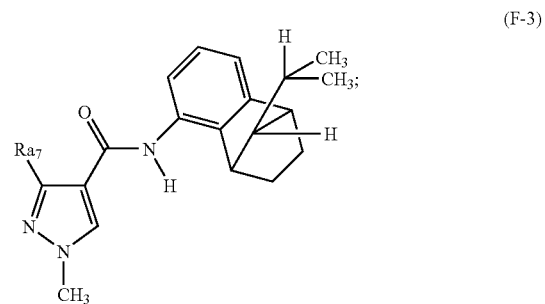

(F-3)

wherein $Ra_7$ is trifluoromethyl or difluoromethyl (WO2004/035589)+TX, the racemic mixture of formula F-4 (anti)

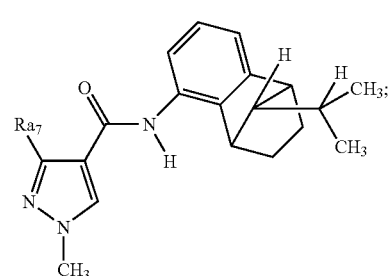

(F-4)

wherein Ra₇ is trifluoromethyl or difluoromethyl (W02004/035589)+TX, the compound of formula F-5

(F-5)

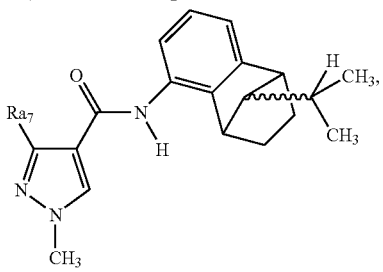

which is an epimeric mixture of racemic compounds of formulae F-3 (syn) and F-4 (anti), wherein the ratio from racemic compounds of formula F-3 (syn) to racemic cmpounds of formula F-4 (anti) is from 1000:1 to 1:1000 and wherein Ra₇ is trifluoromethyl or difluoromethyl (W02004/035589)+TX, the compound of formula F-6

(F-6)

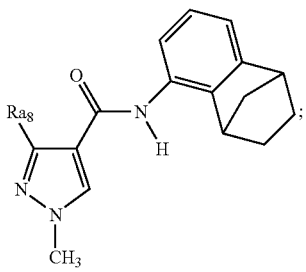

wherein Ra₈ is trifluoromethyl or difluoromethyl (W02004/035589)+TX, the racemic compound of formula F-7 (trans)

(F-7)

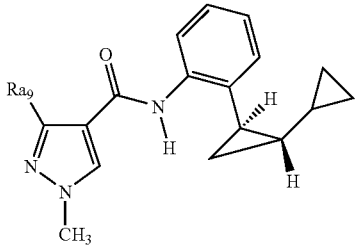

wherein Ra₉ is trifluoromethyl or difluoromethyl (WO03/074491)+TX, the racemic compound of formula F-8 (cis)

(F-8)

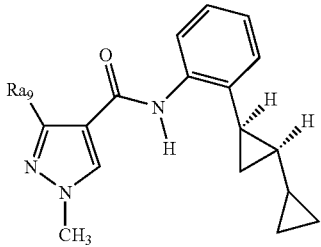

wherein Ra₉ is trifluoromethyl or difluoromethyl (WO03/074491)+TX, the compound of formula F-9

(F-9)

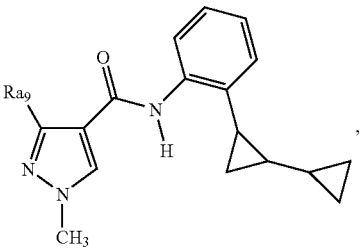

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra₉ is trifluoromethyl or difluoromethyl (WO03/074491)+TX, the compound of formula F-10

(F-10)

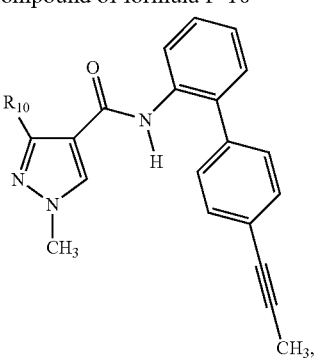

wherein $R_{10}$ is trifluoromethyl or difluoromethyl (W02004/058723)+TX, the racemic compound of formula F-11 (trans)

(F-11)

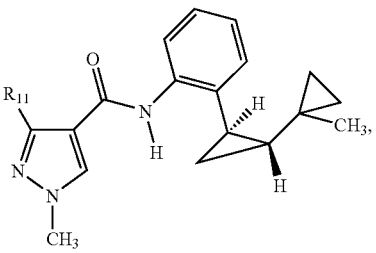

wherein $R_{11}$, is trifluoromethyl or difluoromethyl (WO03/074491)+TX, the racemic compound of formula F-12 (cis)

(F-12)

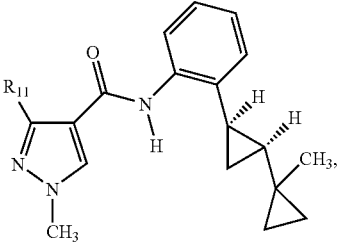

wherein $R_{11}$ is trifluoromethyl or difluoromethyl (WO03/074491)+TX, the compound of formula F-13

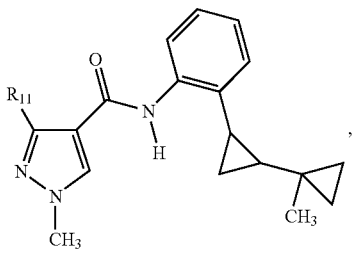

(F-13)

which is a racemic mixture of formulae F-11 (trans) and F-12 (cis), and wherein $R_{11}$ is trifluoromethyl or difluoromethyl (WO 03/074491)+TX, and the compound of formula F-14

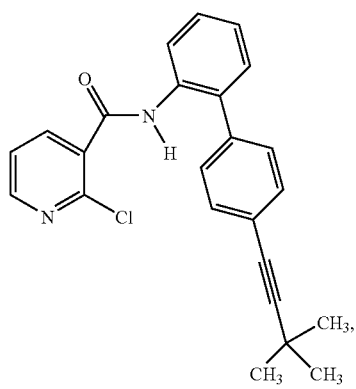

(F-14)

(WO2004/058723)+TX, and the compound of formula F-15

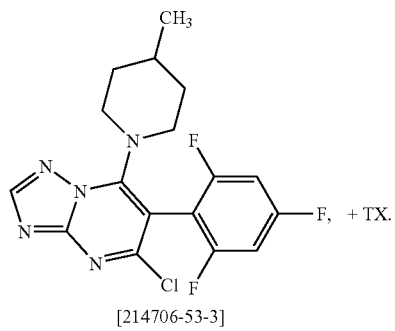

(F-15)

[214706-53-3]

The active ingredient mixture of the compounds of formula I selected from tables A and B with active ingredients described above comprises a compound selected from tables A and B and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables A and B and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables A and B and the active ingredients as described above is not essential for working the present invention.

The references in brackets behind the active ingredients, e.g. [3878-19-1] refer to the Chemical Abstracts Registry number. The compounds of formulae A-1 to A-26 are described in WO 03/015518 or in WO 04/067528. The above described mixing partners are known. Where the active ingredients are included in "The Pesticide Manual" [The Pesticide Manual-A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

BIOLOGICAL EXAMPLES (%=Percent by Weight, Unless Otherwise Specified)

Example B1

Activity Against *Cydia pomonella*

Standard *Cydia* diet cubes (1.5 cm width) are pierced with a tooth-pick and are immersed in liquid paraffin (ca. 80° C.). After the paraffin coat has hardened, an aqueous emulsion containing 400 ppm of active ingredient is applied using a De Vilbis sprayer (25 ml, 1 bar). After the spray coating has dried, the cubes are put into plastic containers which are then populated with two freshly hatched *Cydia pomonella* (1$^{st}$ instar). The containers are then closed with a plastic cap. After 14 days incubation at 26° C. and 40-60% relative humidity, the survival rate of the caterpillars as well as their growth regulation is determined. In this test, compounds listed in Table C above show good activity. In particular compounds A.1.1, A.1.13, A.1.7 and A.1.4 have an activity of over 80%.

Example B2

Activity Against *Diabrotica balteata*

Maize seedlings are sprayed with an aqueous emulsion spray mixture comprising 400 ppm of active ingredient and, after the spray coating has dried on, populated with 10 larvae (2nd instar) of *Diabrotica balteata* and introduced into a plastic container. 6 days later, the percentage reduction in the population (% activity) is determined by comparing the number of dead larvae between the treated and untreated plants.

In this test, compounds listed in Table C above show good activity. In particular compounds A.1.13, A.1.1, A.1.4, B. 1.28, A.1.122 and A.1.7 have an activity of over 80%.

Example B3

Activity against *Heliothis virescens* (foliar application)

Young soya plants are sprayed with an aqueous emulsion spray mixture comprising 400 ppm of active ingredient and, after the spray coating has dried on, populated with 10 caterpillars (1st instar) of Heliothis virescens and introduced into a plastic container. 6 days later, the percentage reduction in the population and in the feeding damage (% activity) are determined by comparing the number of dead caterpillars and the feeding damage between the treated and untreated plants.

In this test, compounds listed in Table C above show good activity. In particular compounds A.1.13, A.1.4, A.1.1 and A.1.7 have an activity of over 80%.

Example B4

Activity Against *Heliothis virescens* (Application to Eggs)

*Heliothis virescens* eggs, which have been deposited on cotton, are sprayed with an aqueous emulsion spray mixture comprising 400 ppm of active ingredient. After 8 days, the percentage hatching rate of the eggs and the survival rate of the caterpillars (% activity) are evaluated in comparison with untreated control batches.

In this test, compounds listed in Table C above show good activity. In particular compounds A.1.13, A.1.1, A.1.4, B. 1.28, A.1.122, A.1.57, A.1.131 and A.1.7 have an activity of over 80%.

Example B5

Activity Against *Myzus Persicae* (Foliar Application)

Pea seedlings are infected with *Myzus persicae*, subsequently sprayed with a spray mixture comprising 400 ppm of active ingredient and then incubated at 20°. 3 and 6 days later, the percentage reduction in the population (% activity) is determined by comparing the number of dead aphids between the treated and untreated plants.

In this test, compounds listed in Table C above show good activity. In particular compounds A.1.13, A.1.4, A.1.122 and A.1.7 have an activity of over 80%.

Example B6

Activity Against *Myzus persicae* (Systemic Application)

Pea seedlings are infected with *Myzus persicae*, and their roots are subsequently placed into a spray mixture comprising 400 ppm of active ingredient. The seedlings are then incubated at 20°. 3 and 6 days later, the percentage reduction in the population (% activity) is determined by comparing the number of dead aphids between the treated and untreated plants. In this test, compounds listed in Table C above show good activity. In particular compounds A.1.4, A.1.122 and A.1.7 have an activity of over 80%.

Example B7

Activity Against *Plutella xylostella*

Young cabbage plants are sprayed with an aqueous emulsion spray mixture comprising 400 ppm of active ingredient and, after the spray coating has dried on, populated with 10 caterpillars (3rd instar) of *Plutella xylostella* and introduced into a plastic container. 3 days later, the percentage reduction in the population and in the feeding damage (% activity) are determined by comparing the number of dead caterpillars and the feeding damage between the treated and untreated plants.

In this test, compounds listed in Table C above show good activity. In particular compounds A.1.13, A.1.1, A.1.4, B. 1.28, A.1.122, A.1.57, A.1.131, A.1.134 and A.1.7 have an activity of over 80%.

Example B8

Activity Against *Spodoptera littoralis*

Young soya plants are sprayed with an aqueous emulsion spray mixture comprising 400 ppm of active ingredient and, after the spray coating has dried on, populated with 10 caterpillars (1st instar) of *Spodoptera littoralis* and introduced into a plastic container. 3 days later, the percentage reduction in the population and in the feeding damage (% activity) are determined by comparing the number of dead caterpillars and the feeding damage between the treated and untreated plants.

In this test, compounds listed in Table C above show good activity. In particular compounds A.1.13, A.1.1, A.1.4, B. 1.28, A.1.122, A.1.57, A.1.131 and A.1.7 have an activity of over 80%.

Example B9

Systemic Insecticide Test for *Spodoptera littoralis* (Cotton Leafworm)

Four day old maize seedlings (*Zea mais*, variety Stoneville) are placed individual in vials containing 24 ml water into which the chemical is diluted at 12.5 ppm. Seedlings are allowed to grow for six days. Subsequently leaves are cut and placed in a Petri dish (5 cm diameter), inoculated with twelve to fifteen 1st instar *S. littoralis* larvae and incubated for four days in a growth chamber (25° C., 50% r.h., 18:6 L:D photo period). Number of alive insects are counted and percentage of dead calculated. Tests were conducted with one replicate.

In this test, compounds listed in Table C above show good activity. In particular compounds A.1.13, A.1.1, A.1.4, A.1.7, A.1.13, A.1.122, A.1.131 and B1.28 have an activity of over 80%.

Example B10

Activity Against *Frankliniella occidentalis*

Bean leaf discs on agar in petri dishes or bean plants in a spray chamber are treated with diluted test solutions. After drying leaf discs are cut and placed in plastic cups on the surface of an agar layer and infested with mixed population. 6 days (leaf discs) or 14 days (plants) after the infestation, samples are checked for reduction of treated population and compared to the non treated population. In this test, compounds listed in Table C above show good activity. In particular compounds A.1.1, A.1.4, A.1.13, A.1.122 and A.1.7 have an activity of over 80%.

What is claimed is:
1. A compound of formula I

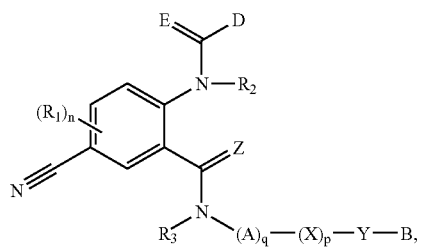

wherein
each of E and Z, which may be the same or different, represents oxygen or sulfur;
A is $C_1$-$C_6$alkylene, $C_2$-$C_6$alkenylene, $C_2$-$C_6$alkynylene, or a bivalent three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms;
and it being possible for the three- to ten-membered ring system itself and also for the $C_1$-$C_6$alkylene, $C_2$-$C_6$alkenylene and $C_2$-$C_6$alkynylene groups to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsutfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino-sulfonyl, N,N-di($C_1$-$C_2$alkyl)aminosulfonyl, di($C_1$-$C_4$alkyl)amino, halogen, cyano or nitro; and substituents at nitrogen atoms in the ring systems being other than halogen;
X is oxygen, NH or $C_1$-$C_4$alkyl-N;
Y is a three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms;
and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino- sulfonyl, N,N-di($C_1$-$C_2$alkyl)amino-sulfonyl, di($C_1$-$C_4$alkyl)amino, halogen, cyano or nitro; and substituents at nitrogen atoms in the ring systems being other than halogen;

p is 0 or 1;

q is 0 or 1;

B is a three- to four-membered ring system which is fully or partially saturated and can contain a hetero atom selected from the group consisting of nitrogen, oxygen and sulfur, and it being possible for the three- to four-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino-sulfonyl, N,N-di($C_1$-$C_2$alkyl)amino-sulfonyl, di($C_1$-$C_4$alkyl)amino, halogen, cyano or nitro; and substituents at nitrogen atoms in the ring systems being other than halogen;

each $R_1$ independently is halogen, nitro, cyano, hydroxy, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, phenyl, benzyl or phenoxy, or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

n is 0, 1, 2 or 3;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

D is phenyl, 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

or D is a group

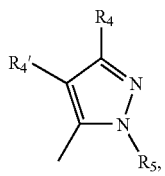  (D₁)

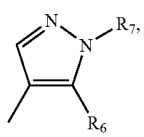  (D₂)

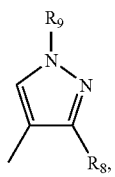  (D₃)

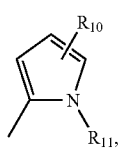  (D₄)

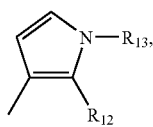  (D₅)

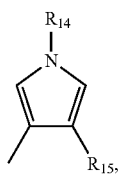  (D₆)

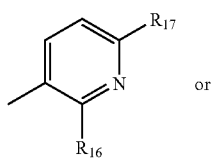  (D₇)

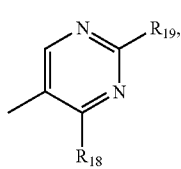  (D₈)

$R_4$, $R_4'$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl or agronomically acceptable salts/stereoisomers/enantiomers/tautomers/N-oxides of those compounds.

2. A compound according to claim 1, wherein $R_4'$ is hydrogen.

3. A pesticidal composition, which comprises at least one compound according to claim 1 of the formula I or, where appropriate, a tautomer thereof, in each case in free form or in agrochemically utilizable salt form, as active ingredient and at least one auxiliary.

4. A composition according to claim 3 for controlling insects or representatives of the order Acarina.

5. A method for controlling pests, which comprises applying a composition according to claim 3 to the pests or their environment.

6. A method according to claim 5 for controlling insects or representatives of the order Acarina.

7. A method according to claim 5 for the protection of plant propagation material from the attack by pests, which comprises treating the propagation material or the site, where the propagation material is planted.

8. Plant propagation material treated in accordance with the method described in claim 7.

9. A process for the preparation of a compound of formula I according to claim 1 or, where appropriate, a tautomer thereof, in each case in free form or in salt form, which comprises a) for the preparation of a compound of formula I, in which $R_2$ is hydrogen and E and Z are oxygen, or, where appropriate, a tautomer and/or salt thereof, reacting a compound of the formula

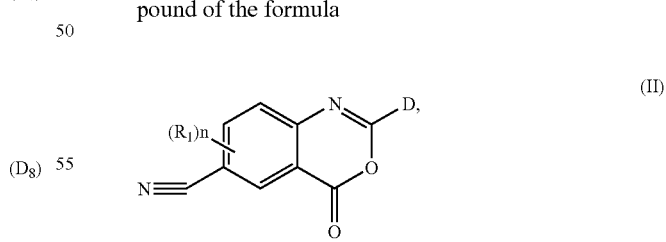  (II)

in which $R_1$, n, and D have the meanings given for the formula I, or, where appropriate, a tautomer and/or salt thereof with a compound of the formula $HN(R_3)$-$(A)_q$-$(X)_p$—Y—B  (III), in which $R_3$, p, q, A, X, Y and B have the meanings given for the formula I, or, where appropriate, with a tautomer and/or salt thereof or, b) for the preparation of a compound of formula I, or, where appropriate, a tautomer and/or salt thereof, reacting a compound of the formula

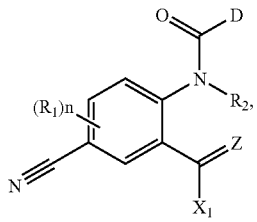 (IV)

in which $R_1$, $R_2$, n, Z and D have the meanings given for the formula I; and $X_1$ is a leaving group, or, where appropriate, a tautomer and/or salt thereof with a compound of the formula $HN(R_3)\text{-}(A)_q\text{-}(X)_q\text{—}Y\text{—}B$ (III), in which $R_3$, p, q, A, X, Y and B have the meanings given for the formula I, or, where appropriate, with a tautomer and/or salt thereof or, c) for the preparation of a compound of formula I, or, where appropriate, a tautomer and/or salt thereof, reacting a compound of the formula

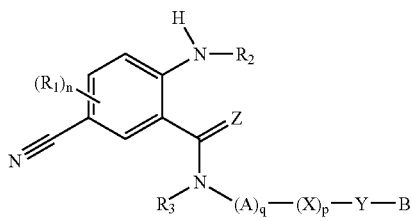 (V)

in which $R_1$, $R_2$, $R_3$, n, p, q, A, X, Y, Z and B have the meanings given for the formula I, or, where appropriate, a tautomer and/or salt thereof with a compound of the formula $X_2C(=O)D$ (VI), in which $R_1$ has the meaning given for the formula I; and $X_2$ is a leaving group, or, where appropriate, with a tautomer and/or salt thereof.

10. A compound of the formula

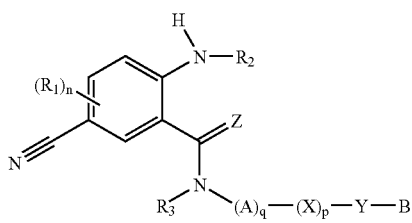 (V)

wherein:

Z is oxygen or sulfur;

A is $C_1$-$C_6$alkylene, $C_2$-$C_6$alkenylene, $C_2$-$C_6$alkynylene, or a bivalent three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms; and it being possible for the three- to ten-membered ring system itself and also for the $C_1$-$C_6$alkylene, $C_2$-$C_6$alkenylene and $C_2$-$C_6$alkynylene groups to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, C-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino- sulfonyl, N,N-di($C_1$-$C_2$alkyl)aminosulfonyl, di($C_1$-$C_4$alkyl)amino, halogen, cyano or nitro; and substituents at nitrogen atoms in the ring systems being other than halogen;

X is oxygen, NH or $C_1$-$C_4$alkyl-N;

Y is a three- to ten-membered monocyclic or fused bicyclic ring system which can be partially saturated or fully saturated and can contain 1 to 4 hetero atoms selected from the group consisting of nitrogen, oxygen and sulfur, it not being possible for each ring system to contain more than 2 oxygen atoms or aiid more than 2 sulfur atoms;

and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$-$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino-sulfonyl, N,N-di($C_1$-$C_2$alkyl)amino-sulfonyl, di($C_1$-$C_4$alkyl)amino, halogen, cyano or nitro; and substituents at nitrogen atoms in the ring systems being other than halogen;

p is 0 or 1;

q is 0 or 1;

B is a three- to four-membered ring system which is fully or partially saturated and can contain a hetero atom selected from the group consisting of nitrogen, oxygen and sulfur, and it being possible for the three- to four-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl, or by a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms or more than 2 sulfur atoms, and it being possible for the three- to ten-membered ring system itself to be mono-, di- or trisubstituted by halogen, cyano, nitro, hydroxy, $C_1$-$C_6$alkyl, $C_2$-$C_6$alkenyl, $C_2$-$C_6$alkynyl, $C_3$-$C_6$cycloalkyl, $C_5$-$C_7$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_6$halocycloalkyl, $C_5$-$C_7$halocycloalkenyl, $C_5$-$C_8$halocycloalkynyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or phenyl, it being possible for the phenyl group in turn to be substituted by hydroxy, $C_1$-$C_6$alkyl, $C_1$-$C_6$haloalkyl, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_4$alkylcarbonyl-$C_1$ -$C_3$alkylthio, $C_2$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylamino-sulfonyl, N,N-di($C_1$-$C_2$alkyl)amino-sulfonyl, di($C_1$-$C_4$alkyl)amino, halogen, cyano or nitro; and substituents at nitrogen atoms in the ring systems being other than halogen;

each $R_1$ independently is halogen, nitro, cyano, hydroxy, $C_1$-$C_6$alkyl, $C_2$-$C_6$alkenyl, $C_2$-$C_6$alkynyl, $C_3$-$C_6$cycloalkyl, $C_2$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, phenyl, benzyl or phenoxy, or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

n is 0, 1, 2 or 3; and each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino.

* * * * *